US012277710B2

United States Patent
Nishide et al.

(10) Patent No.: US 12,277,710 B2
(45) Date of Patent: Apr. 15, 2025

(54) PROGRAM, INFORMATION PROCESSING METHOD, AND INFORMATION PROCESSING DEVICE

(71) Applicant: HOYA CORPORATION, Tokyo (JP)

(72) Inventors: Akihiko Nishide, Tokyo (JP); Junko Sugai, Kanagawa (JP)

(73) Assignee: HOYA CORPORATION, Tokyo (JP)

( * ) Notice: Subject to any disclaimer, the term of this patent is extended or adjusted under 35 U.S.C. 154(b) by 386 days.

(21) Appl. No.: 17/786,321

(22) PCT Filed: Mar. 4, 2021

(86) PCT No.: PCT/JP2021/008409
§ 371 (c)(1),
(2) Date: Jun. 16, 2022

(87) PCT Pub. No.: WO2021/250951
PCT Pub. Date: Dec. 16, 2021

(65) Prior Publication Data
US 2023/0105799 A1    Apr. 6, 2023

(30) Foreign Application Priority Data

Jun. 8, 2020  (JP) ................. 2020-099466

(51) Int. Cl.
G06T 7/00      (2017.01)
A61B 1/005     (2006.01)
G06T 7/73      (2017.01)

(52) U.S. Cl.
CPC .............. *G06T 7/0016* (2013.01); *G06T 7/74* (2017.01); *A61B 1/005* (2013.01);
(Continued)

(58) Field of Classification Search
CPC ..... G06T 7/0016; G06T 7/74; G06T 2200/04; G06T 2207/10068; G06T 2207/10081;
(Continued)

(56) References Cited

U.S. PATENT DOCUMENTS

| 5,762,995 A * | 6/1998 | Kondo | A61M 25/0045 427/178 |
|---|---|---|---|
| 2004/0024288 A1 | 2/2004 | Uchikubo | |
| 2006/0184031 A1* | 8/2006 | Ichioka | A61B 8/483 600/447 |
| 2010/0114546 A1* | 5/2010 | Boyden | G16H 20/10 703/11 |
| 2012/0033105 A1* | 2/2012 | Yoshino | A61B 1/00186 348/E5.051 |

(Continued)

FOREIGN PATENT DOCUMENTS

| JP | 2000-287940 A | 10/2000 |
|---|---|---|
| JP | 2002-238887 A | 8/2002 |

(Continued)

OTHER PUBLICATIONS

International Search Report issued in International Bureau of WIPO Patent Application No. PCT/JP2021/008409, dated May 25, 2021, along with an English translation thereof.

*Primary Examiner* — Negussie Worku
(74) *Attorney, Agent, or Firm* — GREENBLUM & BERNSTEIN, P.L.C.

(57) ABSTRACT

A program causes a computer to perform processing of: acquiring an endoscopic image obtained by capturing a subject using an endoscope; extracting region-of-interest information from the acquired endoscopic image; acquiring a three-dimensional medical image obtained by capturing an inside of a body of the subject using at least one of X-ray CT, X-ray cone beam CT, MRI-CT, and an ultrasonic diagnostic device; deriving position information in a coordinate system of the three-dimensional medical image specified by the region-of-interest information and the three-dimensional medical image; and storing the region-of-interest information and the three-dimensional medical image in association with each other based on the derived position information (Continued)

and a capturing time point of each of the endoscopic image and the three-dimensional medical image.

13 Claims, 20 Drawing Sheets

(52) U.S. Cl.
CPC .............................. *G06T 2200/04* (2013.01); *G06T 2207/10068* (2013.01); *G06T 2207/10081* (2013.01); *G06T 2207/10088* (2013.01); *G06T 2207/10136* (2013.01); *G06T 2207/20081* (2013.01); *G06T 2207/30096* (2013.01)

(58) Field of Classification Search
CPC . G06T 2207/10088; G06T 2207/10136; G06T 2207/20081; G06T 2207/30096; G06T 7/0012; G06T 2207/20084; A61B 1/005; A61B 34/25; A61B 2034/105; A61B 2034/2059; A61B 2090/365; A61B 2562/0219; A61B 2562/0223; A61B 2562/0233; A61B 2562/0247; A61B 2562/0271; A61B 2562/029; A61B 5/055; A61B 6/03; A61B 8/14; G06N 3/0464; G06N 3/084; G16H 30/40; G16H 40/63; G16H 40/67; G16H 50/20; G16H 50/70; G16H 30/20; G06V 2201/031
USPC ........................................................ 382/128
See application file for complete search history.

(56) References Cited

U.S. PATENT DOCUMENTS

| | | | |
|---|---|---|---|
| 2015/0287243 A1* | 10/2015 | Itai | A61B 6/50 |
| | | | 345/419 |
| 2018/0070903 A1* | 3/2018 | Maeda | A61B 6/504 |
| 2018/0211387 A1* | 7/2018 | Wang | A61B 5/02007 |
| 2020/0082579 A1* | 3/2020 | Sekiya | G06T 7/0012 |
| 2020/0187768 A1* | 6/2020 | Shelton | A61B 1/015 |
| 2020/0193602 A1 | 6/2020 | Kamon | |
| 2021/0012495 A1* | 1/2021 | Kamon | G16H 50/20 |
| 2021/0209398 A1* | 7/2021 | Endo | G06T 7/0012 |
| 2021/0219940 A1* | 7/2021 | Abe | G06T 19/20 |
| 2022/0351407 A1* | 11/2022 | Nishide | G06T 7/30 |
| 2022/0401027 A1* | 12/2022 | Mowery | A61B 5/0066 |
| 2023/0162356 A1* | 5/2023 | Horiuchi | A61B 1/00055 |
| | | | 382/128 |
| 2023/0255467 A1* | 8/2023 | Ikenoyama | G06T 7/0012 |
| | | | 382/128 |

FOREIGN PATENT DOCUMENTS

| | | |
|---|---|---|
| JP | 2003-265408 A | 9/2003 |
| JP | 2006-271695 A | 10/2006 |
| JP | 2011-206168 A | 10/2011 |
| JP | 2014-124384 A | 7/2014 |
| WO | 2019/049503 A1 | 3/2019 |
| WO | 2019/130868 A1 | 7/2019 |

* cited by examiner

REGION-OF-INTEREST (ROI) TABLE

| SUBJECT ID | CAPTURING DATE AND TIME OF ENDOSCOPIC IMAGE | ENDOSCOPIC IMAGE | FRAME NUMBER | S COORDINATE (INSERTION DISTANCE) | ROI TYPE | ROI POSITION |
|---|---|---|---|---|---|---|
| YA-002 | 2019.08-01 | ya-19080101.jpg | null | 10 | CLIP | Xa,Ya |
| YA-002 | 2019.08-01 | ya-19080101.jpg | null | 20 | TRACE OF DRUG | Xb,Yb |
| YA-002 | 2019.08-01 | ya-19080101.jpg | null | 30 | CANDIDATE LESION | Xc,Yc |
| YA-002 | 2019.08-01 | ya-190801.avi | 10 | 15 | LESION | Xd,Yd |
| YA-002 | 2019.08-01 | ya-190801.avi | . | . | . | . |
| YA-002 | 2019.08-01 | ya-190801.avi | . | . | . | . |
| YA-002 | 2019.07-25 | ya-180501.jpg | . | . | . | . |
| HI-669 | 2019.04-01 | hi-190401.jpg | . | . | . | . |
| TU-123 | 2019.03-01 | tu-190301.jpg | . | . | . | . |

| THREE-DIMENSIONAL COORDINATE (IN-VIVO COORDINATE) | THREE-DIMENSIONAL MEDICAL IMAGE | CAPTURING DATE AND TIME OF THREE-DIMENSIONAL MEDICAL IMAGE | VIEWPOINT POSITION | VIEWPOINT DIRECTION | VIRTUAL ENDOSCOPIC IMAGE | PIXEL NUMBER |
|---|---|---|---|---|---|---|
| x91,y91,z91 | ya-002-A.dcm | 2019.07-01 | (x10,y10,z10) | (θx10,θy10,θz10) | ya-19080101-VR.jpg | [a1],[b1] |
| x92,y92,z92 | ya-002-A.dcm | 2019.07-01 | (x20,y20,z20) | (θx20,θy20,θz20) | ya-19080102-VR.jpg | [a2],[b2] |
| x93,y93,z93 | ya-002-A.dcm | 2019.07-01 | (x30,y30,z30) | (θx30,θy30,θz30) | ya-19080103-VR.jpg | [a3],[b3] |
| x94,y94,z94 | ya-002-A.dcm | | (x1,y1,z1) | (θx1,θy1,θz1) | ya-190801-1-VR.jpg | [a4],[b4] |

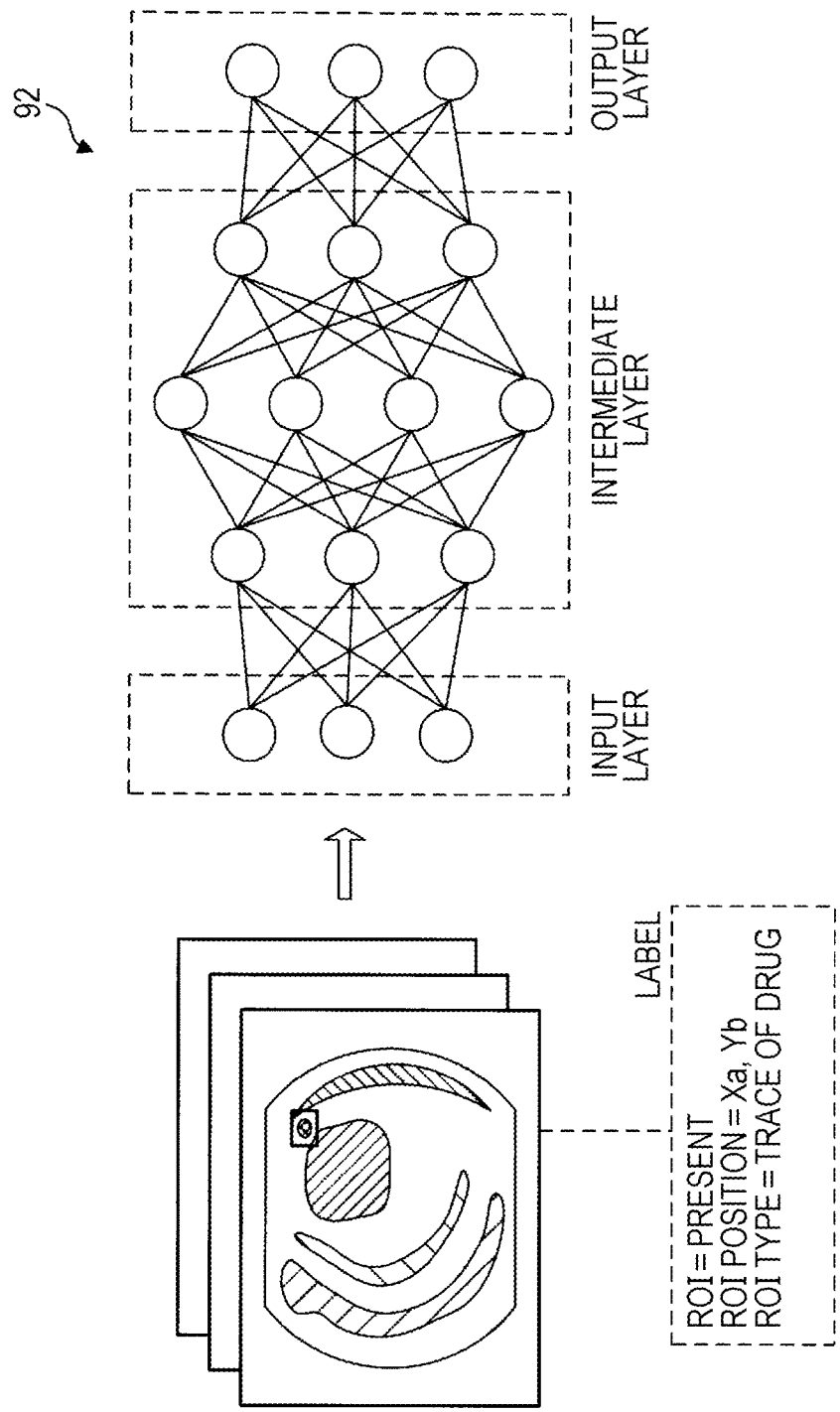

PROGRAM, INFORMATION PROCESSING METHOD, AND INFORMATION PROCESSING DEVICE

TECHNICAL FIELD

The present technology relates to a program, an information processing method, and an information processing device.

The present application claims priority based on Japanese Patent Application No. 2020-099466 filed on Jun. 8, 2020, the entire contents of which are incorporated herein by reference.

BACKGROUND ART

The majority of tumor examinations of patients is conducted by inserting an endoscope into a tubular organ site such as the trachea, the bronchus, the upper digestive tract, the pancreas, the biliary tract, or the intestinal tract, in particular, and by using an image obtained by the inserted endoscope. However, in two-dimensional image information of an endoscopic image, a distance to each pixel is not known, a geometric distortion of the image occurs, and an error in image measurement is large. As a result, it is difficult to provide image diagnosis support information by using only an endoscopic image. On the other hand, a virtual endoscope disclosed in Patent Literature 1 provides a virtual endoscopic image using data of an X-ray computed tomography (CT) image. The virtual endoscopic image is created from a three-dimensional X-ray CT image.

CITATION LIST

Patent Literature

Patent Literature 1: JP 2002-238887 A

SUMMARY OF INVENTION

Technical Problem

However, the virtual endoscope disclosed in Patent Literature 1 simply displays a cross-sectional X-ray CT reconstructed image (virtual endoscopic image), and it is not considered to associate a region of interest, such as a lesion, a candidate lesion, a drug, a treatment tool, and a marker, extracted from the endoscopic image with the three-dimensional X-ray CT image at the time of performing diagnosis support.

In one aspect, an object is to provide a program or the like that efficiently associates a region of interest extracted from an endoscopic image with a three-dimensional medical image.

Solution to Problem

A program according to one aspect of the present disclosure causes a computer to perform processing of: acquiring an endoscopic image obtained by capturing a subject using an endoscope; extracting region-of-interest information from the acquired endoscopic image; acquiring a three-dimensional medical image obtained by capturing an inside of a body of the subject using at least one of X-ray CT, X-ray cone beam CT, MRI-CT, and an ultrasonic diagnostic device; deriving position information in a coordinate system of the three-dimensional medical image specified by the region-of-interest information and the three-dimensional medical image; and storing the region-of-interest information and the three-dimensional medical image in association with each other based on the derived position information and a capturing time point of each of the endoscopic image and the three-dimensional medical image.

An information processing method according to one aspect of the present disclosure includes acquiring an endoscopic image obtained by capturing a subject using an endoscope; extracting region-of-interest information from the acquired endoscopic image; acquiring a three-dimensional medical image obtained by capturing an inside of a body of the subject using at least one of X-ray CT, X-ray cone beam CT, MRI-CT, and an ultrasonic diagnostic device; deriving position information in a coordinate system of the three-dimensional medical image specified by the region-of-interest information and the three-dimensional medical image; and storing the region-of-interest information and the three-dimensional medical image in association with each other based on the derived position information and a capturing time point of each of the endoscopic image and the three-dimensional medical image.

An information processing device according to one aspect of the present disclosure includes: an acquisition unit that acquires an endoscopic image obtained by capturing a subject using an endoscope and a three-dimensional medical image obtained by capturing an inside of a body of the subject using at least one of X-ray CT, X-ray cone beam CT, MRI-CT, and an ultrasonic diagnostic device; an extraction unit that extracts region-of-interest information from the acquired endoscopic image; a deriving unit that derives position information in a coordinate system of the three-dimensional medical image specified by the region-of-interest information and the three-dimensional medical image; and a storage unit that stores the region-of-interest information and the three-dimensional medical image in association with each other based on the derived position information and a capturing time point of each of the endoscopic image and the three-dimensional medical image.

Advantageous Effects of Invention

According to the present disclosure, it is possible to provide the program or the like that efficiently associates the region of interest extracted from the endoscopic image with the three-dimensional medical image.

BRIEF DESCRIPTION OF DRAWINGS

FIG. 5 is an explanatory diagram illustrating a data layout (region-of-interest table) of the endoscopic image DB.

FIG. 6 is an explanatory diagram for describing processing of outputting region-of-interest information using a region-of-interest learning model (second learning model).

FIG. 14 is an explanatory diagram illustrating an aspect of an integrated image display screen.

FIG. 15 is a functional block diagram exemplifying functional units included in a control unit of an information processing device according to a third embodiment (correction).

DESCRIPTION OF EMBODIMENTS

First Embodiment

Figure 1:
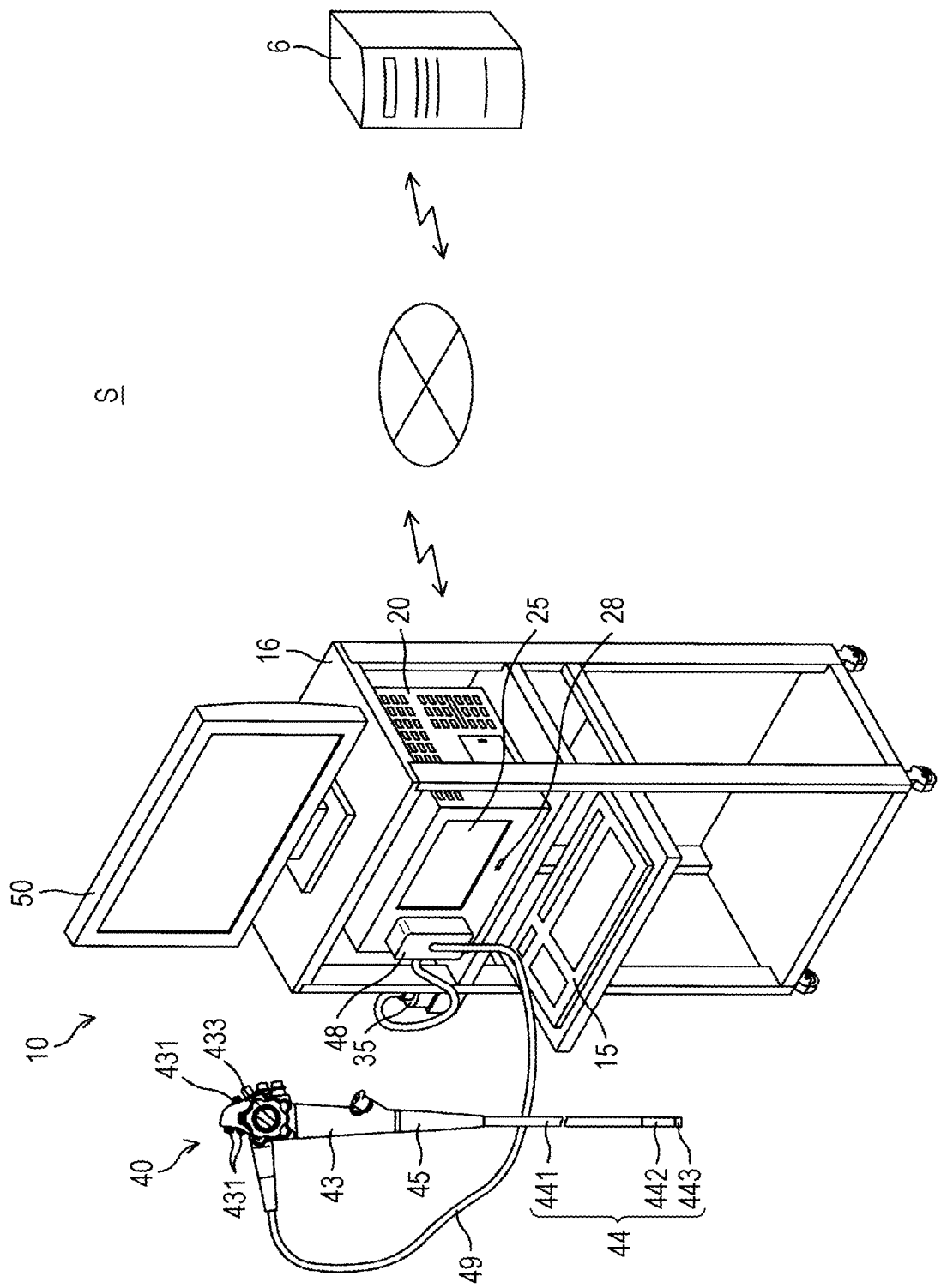
FIG. 1 is a schematic diagram illustrating an outline of a diagnosis support system according to a first embodiment.

Hereinafter, the present invention will be specifically described with reference to the drawings illustrating embodiments of the present invention. FIG. 1 is a schematic diagram illustrating an outline of a diagnosis support system S according to a first embodiment. The diagnosis support system S includes an endoscope device 10 and an information processing device 6 communicatively connected to the endoscope device 10.

The endoscope device 10 transmits an image (captured image) captured by an image sensor of an endoscope 40 to a processor 20 for an endoscope, and the processor 20 for an endoscope performs various types of image processing such as gamma correction, white balance correction, and shading correction, thereby generating endoscopic images set to be easily observed by an operator. The endoscope device 10 outputs (transmits) the generated endoscopic images to the information processing device 6. The information processing device 6 that has acquired the endoscopic images transmitted from the endoscope device 10 performs various types of information processing based on these endoscopic images, and registers the endoscopic images and a three-dimensional medical image acquired from another examination device such as a CT device in an endoscopic image DB 631 (see FIG. 3) in association with each other. When registering the endoscopic image or the like in the endoscopic image DB 631, the information processing device 6 extracts information (region-of-interest information) on a region of interest (ROI) included in the endoscopic image, and registers the endoscopic information in the endoscopic image DB 631 together with the region-of-interest information. The information processing device 6 outputs information regarding diagnosis support (diagnosis support information) based on the endoscopic image, three-dimensional medical image, and region-of-interest information registered in association with each other in the endoscopic image DB 631.

The endoscope device 10 includes the processor 20 for an endoscope, the endoscope 40, and a display device 50. The display device 50 is, for example, a liquid crystal display device or an organic electro luminescence (EL) display device.

The display device 50 is provided on an upper stage of a storage rack 16 with casters. The processor 20 for an endoscope is stored in a middle stage of the storage rack 16. The storage rack 16 is arranged in the vicinity of a bed for an endoscopic examination (not illustrated). The storage rack 16 includes a pull-out shelf on which a keyboard 15 connected to the processor 20 for an endoscope is provided.

The processor 20 for an endoscope has a substantially rectangular parallelepiped shape and is provided with a touch panel 25 on one surface. A reading unit 28 is arranged below the touch panel 25. The reading unit 28 is a connection interface for performing reading and writing on a portable recording medium such as a USB connector, a secure digital (SD) card slot, a compact disc read only memory (CD-ROM) drive, or the like.

The endoscope 40 includes an insertion portion 44, an operation unit 43, a universal cord 49, and a scope connector 48. The operation unit 43 is provided with a control button 431. The insertion portion 44 is long and has one end connected to the operation unit 43 via a bend preventing portion 45. The insertion portion 44 includes a soft portion 441, a bending section 442, and a distal end portion 443 in order from a side of the operation unit 43. The bending section 442 is bent according to an operation of a bending knob 433. Physical detection devices such as a three-axis acceleration sensor, a gyro sensor, a geomagnetic sensor, a magnetic coil sensor, and an endoscope-insertion-type observation device (colonoscope navigation) may be provided on the insertion portion 44. In a case where the endoscope 40 is inserted into a body of a subject, detection results from these physical detection devices may be acquired.

The universal cord 49 is long and has a first end connected to the operation unit 43 and a second end connected to the scope connector 48. The universal cord 49 is soft. The scope connector 48 has a substantially rectangular parallelepiped shape. The scope connector 48 is provided with an air/water supply port 36 (see FIG. 2) for connecting an air/water supply tube.

Figure 2:
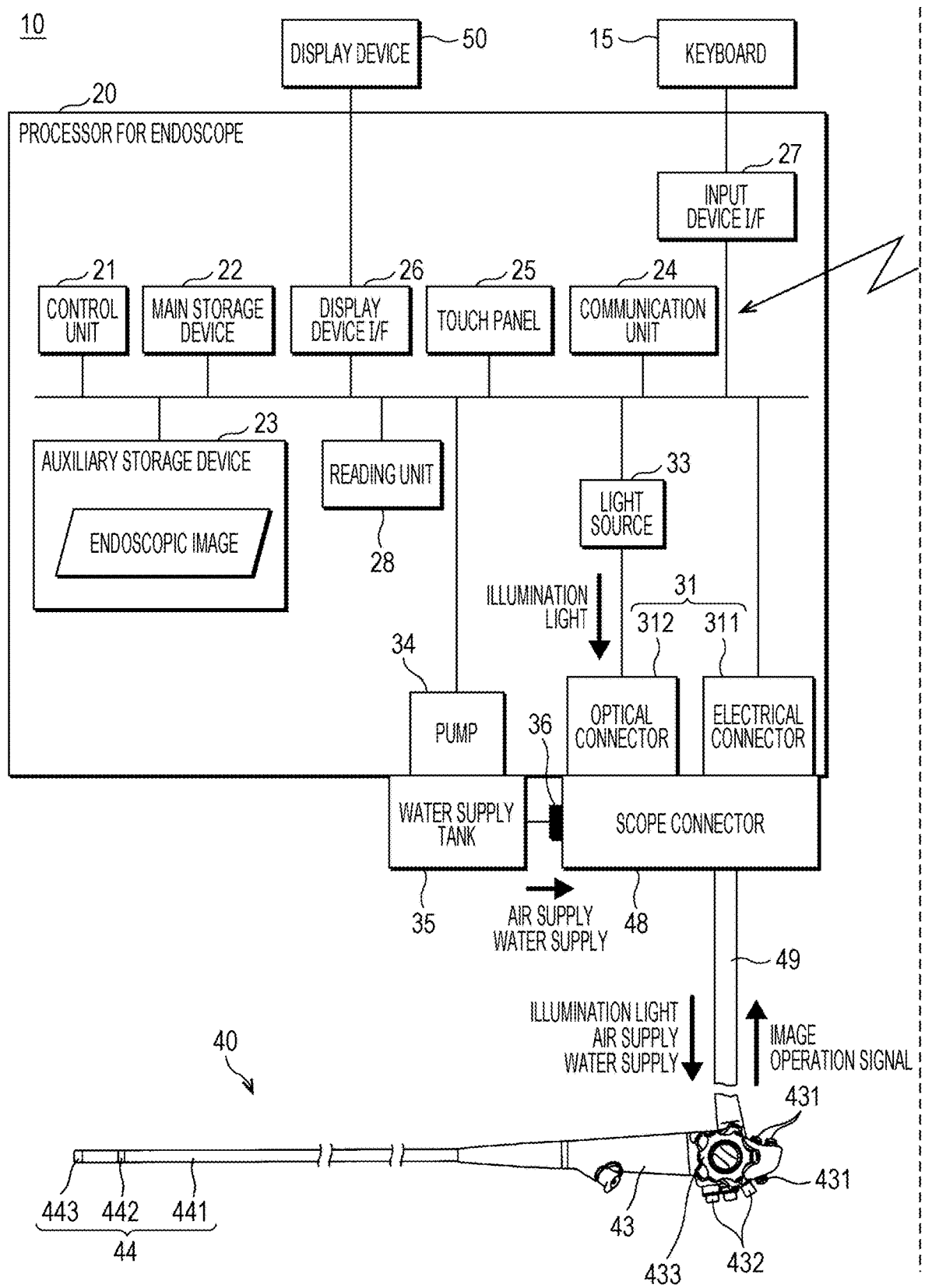
FIG. 2 is a block diagram illustrating a configuration example of an endoscope device included in the diagnosis support system.

FIG. 2 is a block diagram illustrating a configuration example of the endoscope device 10 included in the diagnosis support system S. A control unit 21 is an arithmetic control device that executes a program according to the present embodiment. One or a plurality of central processing units (CPUs), graphics processing units (GPUs), multi-core CPUs, or the like is used for the control unit 21. The control unit 21 is connected to each hardware unit constituting the processor 20 for an endoscope via the bus.

A main storage device 22 is, for example, a storage device such as a static random access memory (SRAM), a dynamic random access memory (DRAM), or a flash memory. The main storage device 22 temporarily stores information necessary in the middle of processing performed by the control unit 21 and a program being executed by the control unit 21. An auxiliary storage device 23 is, for example, a storage device such as an SRAM, a flash memory, or a hard disk and is a storage device having a capacity larger than that of the main storage device 22. In the auxiliary storage device 23, for example, the acquired captured image and the generated endoscopic image may be stored as intermediate data.

A communication unit 24 is a communication module or a communication interface for performing communication with the information processing device 6 via a network in a wired or wireless manner and is, for example, a narrow-area wireless communication module such as Wi-Fi (registered trademark) or Bluetooth (registered trademark) or a wide-area wireless communication module such as 4G, Long Term Evolution (LTE), or 5G. The touch panel 25 includes a display unit such as a liquid crystal display panel and an input unit layered on the display unit. The communication unit 24 may communicate with a CT device, an MRI device (see FIG. 5), or a storage device (not illustrated) that stores data output from these devices.

A display device I/F 26 is an interface for connecting the processor 20 for an endoscope and the display device 50. An input device I/F 27 is an interface for connecting the processor 20 for an endoscope and an input device such as the keyboard 15.

A light source 33 is a high-luminance white light source such as a white LED or a xenon lamp. The light source 33 is connected to the bus via a driver (not illustrated). In the light source 33, turning on, turning off, and a change of luminance are controlled by the control unit 21. Illumination light emitted from the light source 33 is incident on an optical connector 312. The optical connector 312 engages with the scope connector 48 to supply the illumination light to the endoscope 40.

A pump 34 generates a pressure for the air supply and water supply function of the endoscope 40. The pump 34 is connected to the bus via a driver (not illustrated). In the pump 34, turning on, turning off, and a change of the pressure are controlled by the control unit 21. The pump 34 is connected to the air/water supply port 36 provided in the scope connector 48 via a water supply tank 35.

An outline of functions of the endoscope 40 connected to the processor 20 for an endoscope will be described. A fiber bundle, a cable bundle, an air supply tube, a water supply tube, and the like are inserted inside the scope connector 48, the universal cord 49, the operation unit 43, and the insertion portion 44. The illumination light emitted from the light source 33 is emitted from an illumination window provided at the distal end portion 443 via the optical connector 312 and the fiber bundle. The image sensor provided at the distal end portion 443 captures an image of a range illuminated by the illumination light. The captured image is transmitted from the image sensor to the processor 20 for an endoscope via the cable bundle and an electrical connector 311.

The control unit 21 of the processor 20 for an endoscope functions as an image processing unit 211 (see FIG. 7) by executing a program stored in the main storage device 22. The image processing unit 211 performs various types of image processing such as gamma correction, white balance correction, and shading correction on the image (captured image) output from the endoscope 40 and outputs the image as the endoscopic image.

Figure 3:
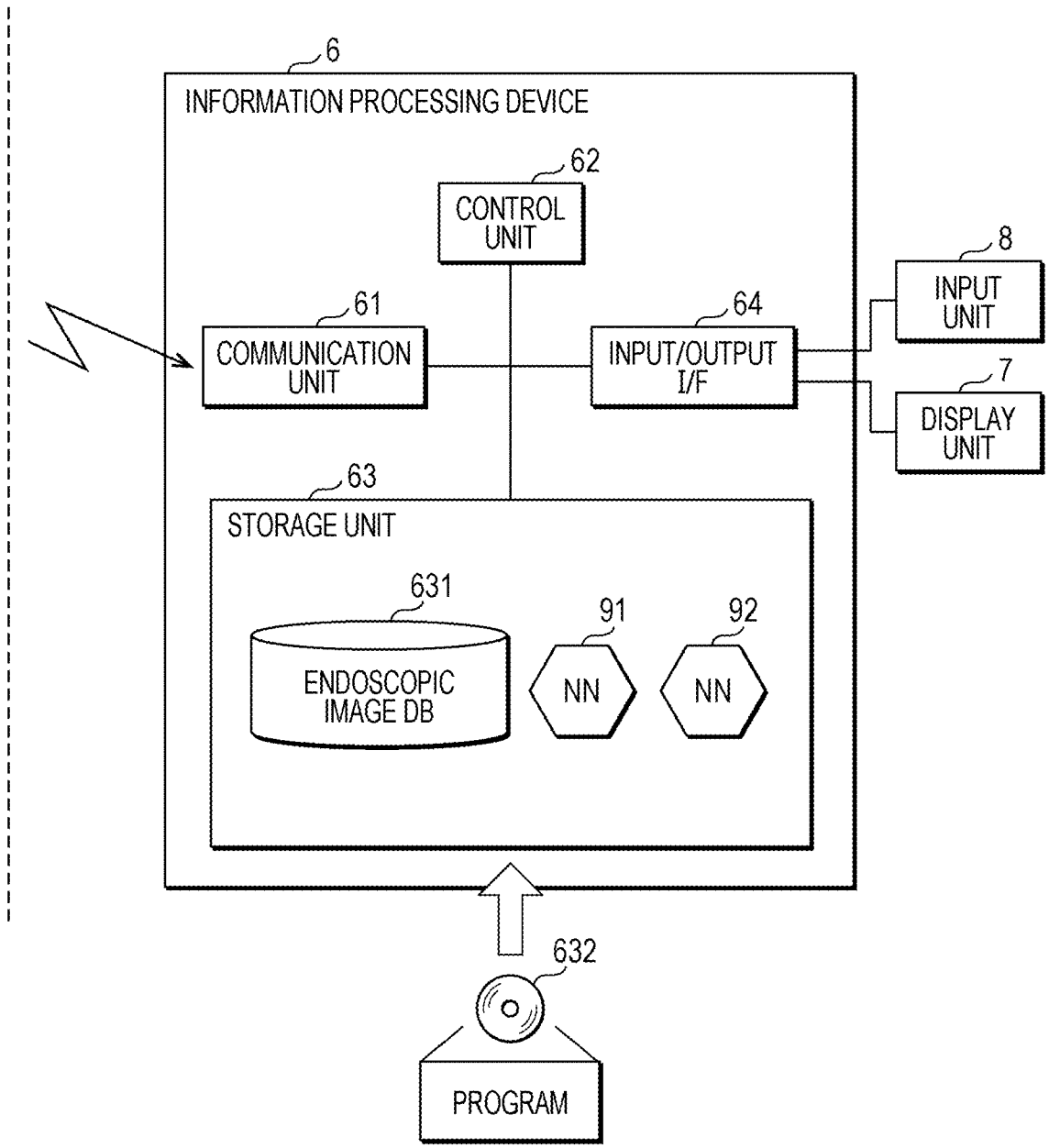
FIG. 3 is a block diagram illustrating a configuration example of an information processing device included in the diagnosis support system.

FIG. 3 is a block diagram illustrating a configuration example of the information processing device 6 included in the diagnosis support system S. The information processing device 6 includes a control unit 62, a communication unit 61, a storage unit 63, and an input/output I/F 64. The information processing device 6 is, for example, a server device, a personal computer, or the like. The server device includes not only a single server device but also a cloud server device or a virtual server device including a plurality of computers. The information processing device 6 may be provided as a cloud server located on an external network accessible from the processor 20 for an endoscope.

The control unit 62 includes one or a plurality of arithmetic processing devices having a time counting function, such as central processing units (CPUs), micro-processing units (MPUs), and graphics processing units (GPUs), and performs various types of information processing, control processing, and the like related to the information processing device 6 by reading and executing a program P stored in the storage unit 63. Alternatively, the control unit 62 may include a quantum computer chip, and the information processing device 6 may be a quantum computer.

The storage unit 63 includes a volatile storage area such as a static random access memory (SRAM), a dynamic random access memory (DRAM), or a flash memory and a nonvolatile storage area such as an EEPROM or a hard disk. The storage unit 63 stores in advance the program P and data to be referred to at the time of processing. The program P stored in the storage unit 63 may be a program P which is stored by being read from a recording medium 632 readable by the information processing device 6. In addition, the program P may be a program which is downloaded from an external computer (not illustrated) connected to a communication network (not illustrated) and is stored in the storage unit 63. The storage unit 63 stores an entity file (instance file of a neural network (NN)) constituting a learning model 9 to be described later. These entity files may be configured as a part of the program P. The storage unit 63 may store the endoscopic image DB 631 (DataBase) to be described later and learning models using the neural network such as a diagnosis support learning model 91 and a region-of-interest learning model 92.

The communication unit 61 is a communication module or a communication interface for performing communication with the endoscope device 10 in a wired or wireless manner and is, for example, a narrow-area wireless communication module such as Wi-Fi (registered trademark) or Bluetooth (registered trademark) or a wide-area wireless communication module such as 4G, LTE, or 5G. The communication unit 61 may communicate with a CT device, an MRI device, or a storage device (not illustrated) that stores data output from these devices.

The input/output I/F 64 is a communication interface conforming, for example, to a communication standard such as USB or DSUB and is a communication interface for performing serial communication with an external device connected to the input/output I/F 64. For example, a display unit 7 such as a display and an input unit 8 such as a mouse or a keyboard are connected to the input/output I/F 64, and the control unit 62 outputs, to the display unit 7, a result of information processing performed based on an execution command or an event input from the input unit 8.

Figure 4:
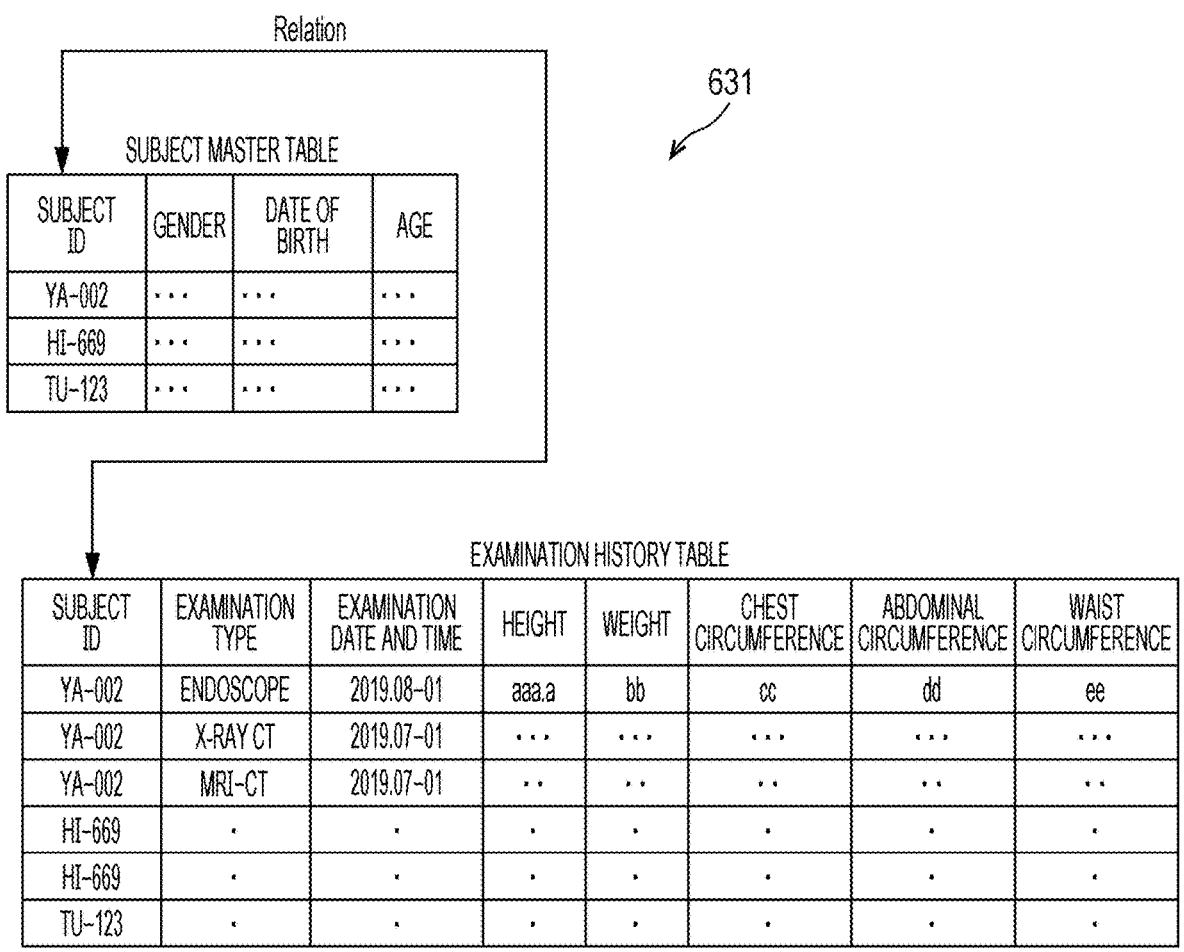
FIG. 4 is an explanatory diagram exemplifying a data layout (subject master table or the like) of an endoscopic image DB.

FIG. 4 is an explanatory diagram exemplifying a data layout (subject master table or the like) of the endoscopic image DB 631. FIG. 5 is an explanatory diagram illustrating a data layout (region-of-interest table) of the endoscopic image DB 631. The endoscopic image DB 631 is stored in the storage unit 63 of the information processing device 6, and is configured by database management software such as a relational database management system (RDBMS) implemented in the information processing device 6. Alternatively, the endoscopic image DB 631 may be stored in a predetermined storage area accessible from the information processing device 6, such as a storage device which is communicatively connected to the information processing device 6. Alternatively, the endoscopic image DB 631 may be stored in the main storage device 22 of the endoscope device 10. That is, the predetermined storage area includes the storage unit 63 of the information processing device 6, the main storage device 22 of the endoscope device 10, and a storage device accessible from the information processing device 6 or the endoscope device 10. The information processing device 6 may acquire the endoscopic image which is output by the processor 20 for an endoscope, an examination date and time, and attribute information of the subject, and register the acquired endoscopic image, the acquired examination date and time, and the acquired attribute information of the subject in the endoscopic image DB 631. Alternatively, the endoscopic image which is directly output from the processor 20 for an endoscope, the examination date and time, and the attribute information of the subject may be directly registered in the endoscopic image DB 631.

The endoscopic image DB 631 includes, for example, the subject master table, an examination history table, and the region-of-interest table, and the subject master table, the examination history table, and the region-of-interest table are normalized in association with a subject ID that is an item (metadata) that is included in common in these tables.

The subject master table includes, for example, the subject ID, a gender, a date of birth, and an age as management items (metadata). In the item (field) of the subject ID, ID information is stored to uniquely identify a subject who has undergone an endoscopic examination. In the items (fields) of the gender and the date of birth, biological attributes including the gender and the date of birth corresponding to the subject ID are stored. In the item (field) of the age, the age at a current time point calculated based on the date of birth is stored. The gender and the age are managed as biological information of the subject by the subject master table.

The examination history table includes, for example, the subject ID, an examination type, an examination date and time, and physique information as management items (metadata). As an example of the physique information in the present embodiment, the physique information includes a height, a weight, a chest circumference, an abdominal circumference, and a waist circumference.

In the item (field) of the subject ID, a value of each subject ID is stored to be associated with the biological attribute of the subject managed in the subject master table.

In the item (field) of the examination type, a type of an examination received by a subject is stored. The type of the examination is, for example, an endoscopic examination, an X-ray CT examination, or an MRI-CT examination, and examination result images (an endoscopic image, an X-ray CT image, and an MRI-CT image) captured by the respective examination devices are generated as results of these examinations.

In the item (field) of the examination date and time, a date and time (examination date and time) when each examination has been performed, that is, a capturing date and time of the examination result image captured by each of the examination devices.

In the respective items (fields) of the physique information including the height, the weight, the chest circumference, the abdominal circumference, and the waist circumference, physique information of a subject at an examination date and time, that is, at a time point when each examination has been performed is stored. Even when different types of examinations, such as the endoscopic examination and the X-ray CT examination, are performed on the same subject, the examinations are performed on the same intracorporeal site of the subject. There is a case where the individual examinations are performed with a predetermined elapsed period interposed therebetween, and a change in physique of a subject during the elapsed period is also assumable. On the other hand, when the physique information of the subject in dates and time when the individual examinations have been performed (examination dates and time) are stored in the examination history table and managed, it is possible to derive a change amount of the physique of the subject in the elapsed period and correct position information to be used at the time of matching the examination result images captured by the respective examination devices with each other based on the change amount. Such correction processing of the position information will be described later.

The region-of-interest table includes the subject ID, an endoscopic image capturing date and time, an endoscopic image, a frame number, an S coordinate (insertion distance), an ROI type, an ROI position, a three-dimensional coordinate (in-vivo coordinate), a three-dimensional medical image, a three-dimensional medical image capturing date and time, a viewpoint position, a viewpoint direction, a virtual endoscopic image, and a pixel number.

In the item (field) of the subject ID, a value of each subject ID is stored to be associated with the biological attribute of the subject managed in the subject master table.

In the item (field) of the endoscopic image capturing date and time, a date and time when the subject corresponding to the subject ID has undergone the endoscopic examination is stored.

In the item (field) of the endoscopic image, the endoscopic image corresponding to the subject ID is stored as object data. The endoscopic image may be a still image in, for example, a jpeg format with one frame or a moving image in, for example, an avi format with several frames. In the item (field) of the endoscopic image, information indicating a storage location (file path) of the endoscopic image stored as a file may be stored.

In a case where the endoscopic image is a moving image, a frame number of the moving image is stored in the item (field) of the frame number. Even in the case of being a moving image, the endoscopic image can be handled in the same manner as a still image by storing the frame number of the moving image, and can be associated with position information (a coordinate in an in-vivo coordinate system) of a three-dimensional medical image or a virtual endoscopic image to be described later.

In the item (field) of the S coordinate (insertion distance), the insertion distance of the endoscope 40 at a capturing time point of the endoscopic image stored in the same record is stored as a value of the S coordinate. Deriving of the insertion distance (S coordinate) or the like will be described later.

In the item (field) of the ROI type, a type of a region of interest (ROI) included in the corresponding endoscopic image is stored. Examples of the type of the region of interest (ROI) include a clip, a trace of drug, a candidate lesion, and lesions. In the item (field) of the ROI position, a position of the region of interest (ROI) included in the corresponding endoscopic image is stored. The position of the region of interest (ROI) is, for example, a coordinate value in a two-dimensional coordinate system of the endoscopic image. The coordinate value may indicate a specific point or a predetermined range. The items (fields) of the region-of-interest information stored in the region-of-interest table are not limited to the ROI type and the ROI position, and may include, for example, items (fields) for storing a name of an intracorporeal site where a region of interest (ROI) is located, diagnosis support information for the region of interest (ROI), and the like.

In the item (field) of the three-dimensional coordinate (in-vivo coordinate), a three-dimensional coordinate (in-vivo coordinate) corresponding to the position of the region of interest (ROI) included in the endoscopic image is stored. The in-vivo coordinate is a coordinate in a three-dimensional coordinate system determined based on a three-dimensional medical image to be described later.

In the item (field) of the three-dimensional medical image, for example, a three-dimensional medical image in a digital imaging and communications in medicine (DICOM) format is stored as object data, the three-dimensional medical image being generated based on data output from a CT device (X-ray CT, X-ray cone beam CT) or an MRI device (MRI-CT). Alternatively, in the item (field) of the three-dimensional medical image, information indicating a storage location (file path) of the three-dimensional medical image stored as a file may be stored.

In the item (field) of the three-dimensional medical image capturing date and time, a date and time when the subject corresponding to the subject ID has undergone the examination such as X-ray CT is stored. That is, a capturing date of tomographic image data such as an X-ray CT image or an MRI-CT image, which is original data of a three-dimensional medical image, is stored at the time of constructing the three-dimensional medical image.

In the item (field) of the viewpoint position, a coordinate of the endoscope 40 in the body at a time point when the endoscopic image is captured, that is, a coordinate of the three-dimensional medical image in the coordinate system are stored. Deriving of the viewpoint position will be described later.

In the item (field) of the viewpoint direction, an orientation of the endoscope 40 at a time point when the endoscopic image is captured, that is, a rotation angle in a coordinate system (the coordinate in the in-vivo coordinate system) of the three-dimensional medical image is stored. Deriving of the viewpoint direction will be described later.

In the item (field) of the virtual endoscopic image, the virtual endoscopic image generated from the three-dimensional medical image is stored as object data. In the item (field) of the virtual endoscopic image, information indicating a storage location (file path) of the virtual endoscopic image stored as a file may be stored. The virtual endoscopic image is generated from the three-dimensional medical image in order to perform matching processing with the endoscopic image. For example, a virtual endoscopic image having the highest degree of matching with the endoscopic image is registered in the same record as the endoscopic image. Generation of the virtual endoscopic image will be described later.

In the item (field) of the pixel number, a pixel number for indicating a position on the virtual endoscopic image corresponding to the position of the region of interest (ROI) included in the endoscopic image is stored. The pixel number is defined in a format of a two-dimensional array, for example. The pixel number may be an array value specifying any pixel, or may be a range of array values for specifying a plurality of pixels.

FIG. 6 is an explanatory diagram for describing processing of outputting region-of-interest information using the region-of-interest learning model 92 (second learning model). The information processing device 6 constructs (generates) a neural network that receives an input of an endoscopic image and outputs region-of-interest information by performing learning based on training data with the endoscopic image as problem data and the region-of-interest information including at least one of presence or absence of the region of interest (ROI), the type of the region of interest (ROI), the position of the region of interest (ROI) (a coordinate range of an image region corresponding to the region of interest), and the like as answer data.

The region-of-interest information included in the problem data may further include a name of an intracorporeal site as a region of interest, such as large intestine colon, stomach, duodenum, or esophagus. The training data also includes an endoscopic image in a state of being diagnosed that there is no region of interest (ROI). The endoscopic image includes, for example, an intracorporeal site to which a therapeutic clip has been applied, an intracorporeal site having a trace of drug administered in the past, an intracorporeal site of a candidate lesion, and an intracorporeal site of a lesion, and these intracorporeal sites are treated as regions of interest (ROI). The answer data includes information labeled according to types of these regions of interest (ROI). The image region corresponding to the region of interest (ROI) may be extracted using a model visualization method such as gradient-weighted class activation mapping (Grad-CAM).

The neural network (region-of-interest learning model 92) learned using the training data is assumed to be used as a program module that is a part of artificial intelligence software. The region-of-interest learning model 92 is used in the information processing device 6 including the control unit 62 (CPU or the like) and the storage unit 63 as described above, and is executed by the information processing device 6 having arithmetic processing capability, whereby a neural network system is configured. That is, the control unit 62 of the information processing device 6 operates to perform an arithmetic operation of extracting a feature amount of the endoscopic image input into an input layer according to a command from the region-of-interest learning model 92 stored in the storage unit 63 and output the region-of-interest information including the presence or absence of the region of interest (ROI) from an output layer.

The input layer has a plurality of neurons that receives the input of a pixel value of the endoscopic image, and the input layer transmits the input pixel value to an intermediate layer. The intermediate layer has a plurality of neurons that extracts an image feature amount of the endoscopic image, and the intermediate layer transfers the extracted image feature amount to the output layer. The output layer has one or a plurality of neurons that output the region-of-interest information including the type of the region of interest (ROI) and the like, and outputs the region-of-interest information based on the image feature amount output from the intermediate layer.

For example, in a case where the region-of-interest learning model 92 is a convolutional neural network (CNN), the intermediate layer has a configuration in which a convolution layer that convolves the pixel value of each pixel input from the input layer and a pooling layer that maps (compresses) the pixel value convolved by the convolution layer are alternately connected, and the intermediate layer finally extracts the feature amount of the endoscopic image while compressing pixel information of the endoscopic image. The output layer has one or a plurality of neurons that output the region-of-interest information in an intracorporeal site included in the endoscopic image, and outputs the region-of-interest information based on the image feature amount or the like output from the intermediate layer.

In the present embodiment, data input into the region-of-interest learning model 92 is described as the endoscopic image, but the present invention is not limited thereto. The data input into the region-of-interest learning model 92 may be a captured image (raw image) captured by the image sensor of the endoscope 40. That is, the region-of-interest learning model 92 may output the region-of-interest information when the captured image is input.

In the present embodiment, the region-of-interest learning model 92 is described as a neural network (NN) such as CNN, but the region-of-interest learning model 92 is not limited to the NN and may be a region-of-interest learning model 92 including another learning algorithm such as a support vector machine (SVM), a Bayesian network, or a regression tree. Alternatively, the region-of-interest learning model 92 may use any object detection algorithm having a function of a segmentation network such as LSTM, RNN, regions with convolutional neural network (RCNN), Fast RCNN, Faster RCNN, single shot multibox detector (SSD), or You Only Look Once (YOLO).

The information processing device 6 compares a value output from the output layer with the region-of-interest information (the presence or absence, type, and position of the region of interest (ROI)) labeled for the problem data (endoscopic image), that is, a correct answer value (answer data), and optimizes a parameter used for the arithmetic processing in the intermediate layer such that the output value from the output layer approaches the correct answer value. The parameter is, for example, a weight (coupling coefficient) between neurons, a coefficient of an activation function used in each neuron, or the like. A parameter optimization method is not particularly limited, but for example, the information processing device 6 optimizes various parameters using a back propagation method. The information processing device 6 performs the above processing on the endoscopic image included in the training data, generates the region-of-interest learning model 92, and stores the generated region-of-interest learning model 92 in the storage unit 63.

The endoscopic image (problem data) used as the training data and the region-of-interest information (answer data) correlated with these pieces of information are stored in a large amount as result data of an endoscopic examination performed in each medical institution, and these pieces of result data can be used to generate a large amount of training data for learning the region-of-interest learning model 92.

Figure 7:
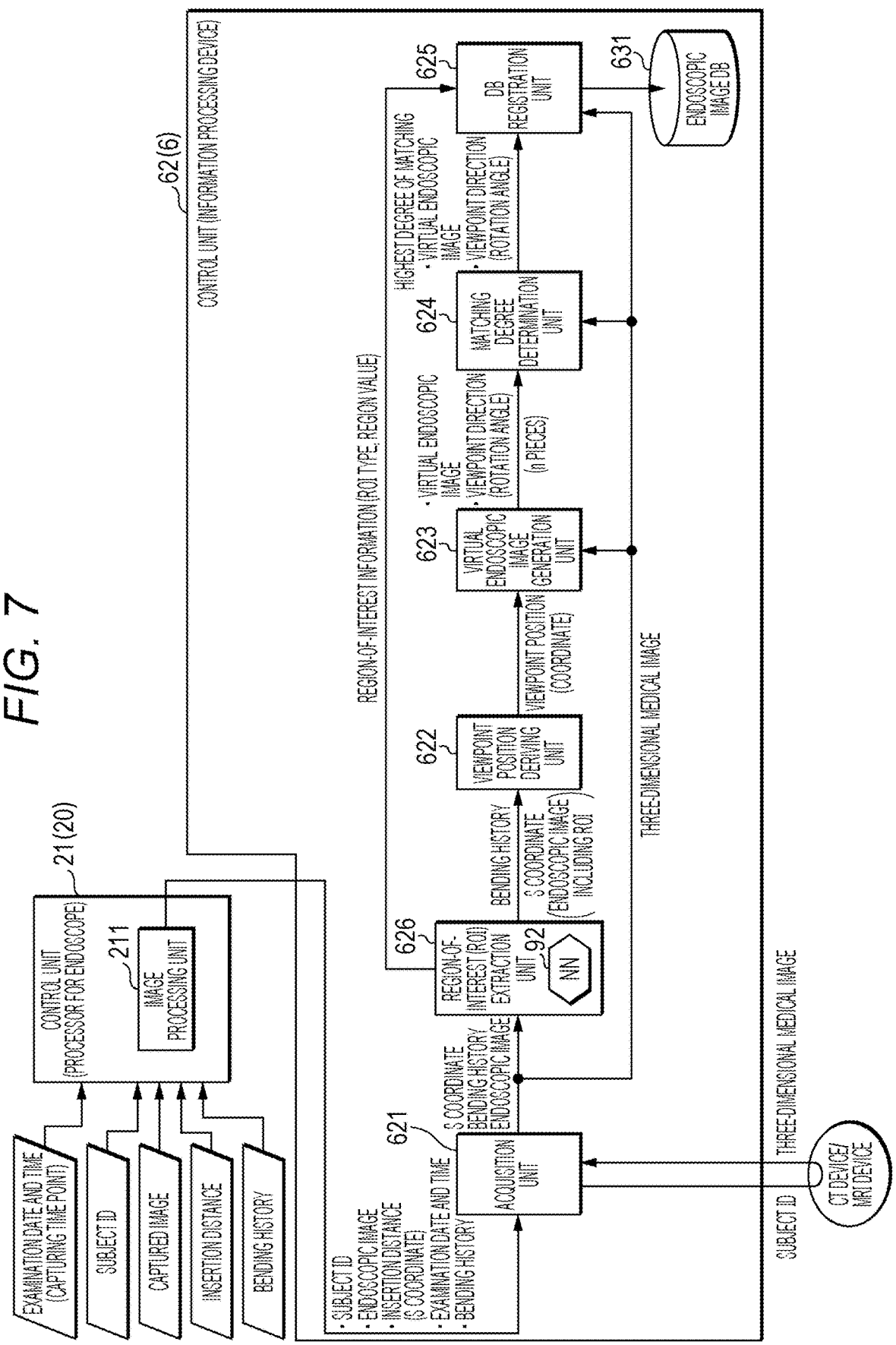
FIG. 7 is a functional block diagram exemplifying functional units included in a control unit of the information processing device.

FIG. 7 is a functional block diagram exemplifying functional units included in the control unit 62 of the information processing device 6. The control unit 21 of the processor 20 for an endoscope (endoscope device 10) executes the program stored in the main storage device 22, thereby functioning as the image processing unit 211. The control unit 62 of the information processing device 6 executes the program P stored in the storage unit 63 to function as an acquisition unit 621, a region-of-interest extraction unit 626, the region-of-interest learning model 92, a viewpoint position deriving unit 622, a virtual endoscopic image generation unit 623, a matching degree determination unit 624, and a DB registration unit 625.

The image processing unit 211 of the processor 20 for an endoscope performs various types of image processing such as gamma correction, white balance correction, and shading correction on the image (captured image) output from the endoscope, and outputs the image as the endoscopic image. The image processing unit 211 outputs (transmits) the generated endoscopic image and the examination date and time based on a capturing time point of the endoscopic image to the information processing device 6. The image processing unit 211 may further output the subject ID which is input from the keyboard 15 to the information processing device 6. The image processing unit 211 may output, to the information processing device 6, information regarding the insertion distance (S coordinate) and bending history information of the endoscope 40 output from a sensor or the like arranged in the insertion portion 44 (flexible tube) of the endoscope 40 in order to measure a surrounding environment of the endoscope 40. The image processing unit 211 may superimpose the information regarding the insertion distance (S coordinate) and the bending history information of the endoscope 40 acquired from the sensor, for example, on the endoscopic image and display the superimposed image on the display device.

Examples of the sensor for acquiring the S coordinate, which is the distance by which the endoscope 40 is inserted into the body, include a temperature sensor, an optical sensor, a pressure sensor, a wetting sensor (electrode), and a humidity sensor. For example, in a case where the sensor is an optical sensor, the optical sensor is arranged inside the insertion portion 44 (flexible tube). On the other hand, the optical sensor can receive light even in a case where the insertion portion 44 (flexible tube) is inserted into the body. Therefore, it is possible to determine that a portion where the optical sensor receives more light is outside the body and a portion where the optical sensor receives less light is inside the body. Then, the control unit 21 of the processor 20 for an endoscope can derive the S coordinate, which is the distance (length) by which the insertion portion 44 (flexible tube) is inserted into the body by specifying the optical sensor that is located at a boundary position which is a body cavity insertion site based on a signal obtained by the optical sensor.

A roller encoder is attached to a mouthpiece (not illustrated) or the like that is in contact with the insertion portion 44 (flexible tube), and the roller encoder rotates by the distance by which the insertion portion 44 (flexible tube) is inserted into the body, whereby the S coordinate, which is the distance by which the endoscope 40 is inserted into the body, can be acquired. The roller encoder of the mouthpiece or the like rotates as the insertion portion 44 (flexible tube) moves forward and backward, and can measure a length between the distal end portion 443 of the endoscope 40 inserted into the body and an opening portion communicating with a lumen of a mouth, a nose, or the like, that is, the insertion distance of the insertion portion 44 (flexible tube). The roller encoder is electrically connected to the processor 20 for an endoscope, and transmits the measured distance to the processor 20 for an endoscope. In addition, an optical encoder may be used instead of the roller encoder.

In addition, in a case where an auxiliary device that measures the insertion distance of the endoscope 40 is attached to the body cavity insertion site which is an entrance of the subject, it is possible to acquire the S coordinate, which is the distance by which the endoscope 40 is inserted into the body, by measuring a passing distance of the endoscope 40. The auxiliary device may be, for example, a device that measures a distance using a scale of a magnetic field such as a linear scale attached to the insertion portion (flexible tube) 44 and a linear head attached to a mouthpiece, or may be a mouthpiece of the endoscope 40 to which a roller is attached. Note that, in a case where the endoscope is inserted into a nose, an anus, or the like, an auxiliary device provided with a roller that is similar to the mouthpiece may be used. Furthermore, a chip in which the insertion distance is recorded at regular intervals may be incorporated in the insertion portion (flexible tube) 44 of the endoscope 40. The processor 20 for an endoscope can acquire the S coordinate, which is the distance by which the endoscope 40 is inserted into the body, from S coordinate information recorded in the chip obtained by the mouthpiece or the like.

The control unit 21 of the processor 20 for an endoscope acquires bending history information of the endoscope 40 inserted into the body, and determines an insertion situation of the endoscope 40 according to the acquired bending history information. The control unit 21 of the processor 20 for an endoscope may detect the bending history information using, for example, an endoscope insertion shape detection device (not illustrated) connected to the processor 20 for an endoscope. For example, as disclosed in JP 2019-37643 A, the endoscope insertion shape detection device may be a device in which a plurality of magnetic coils are arranged inside the insertion portion 44 of the endoscope 40 at predetermined intervals along a longitudinal direction of the insertion portion 44. The bending history information indicates a physical parameter or information regarding bending such as a bending angle or a bending direction.

The acquisition unit 621 acquires the subject ID, the examination date and time, the endoscopic image, the S coordinate (insertion distance), and the bending history information output by the processor 20 for an endoscope. The acquisition unit 621 acquires a three-dimensional medical image of the subject output from the communicatively connected CT device or MRI device based on the acquired subject ID. In a case where the three-dimensional medical image output from another examination device such as the CT device or the MRI device has already been stored in, for example, an external server (not illustrated), the information processing device 6 may access the external server and acquire the three-dimensional medical image of the subject based on the subject ID output from the processor 20 for an endoscope. The acquisition unit 621 outputs the acquired endoscopic image, S coordinate, and the like to the region-of-interest extraction unit 626.

Examples of the three-dimensional medical image include an image represented by volume data constructed from tomographic data output from the CT device, the MRI device, or the like, and an image represented by volume data output from an X-ray cone beam CT device using a Multi Slice (MS) CT device and an X-ray flat panel. In a case where the X-ray CT device or the cone beam CT device is used, the three-dimensional medical image may be, for example, an image in which a composition (body composition) of each pixel of the three-dimensional medical image can be identified by an effective atomic number (effective-Z) by performing dual energy CT (DECT) imaging. In a case where the MRI device is used, the three-dimensional medical image may be an image to which information regarding a composition (body composition) of each pixel of the three-dimensional medical image such as fat or lactic acid is added.

The three-dimensional medical image is, for example, an image represented by volume data including tomographic image data, which is output from a means capable of capturing a three-dimensional image of the inside of the body, such as a CT device, a cone beam CT device, an MRI device, and an ultrasonic diagnostic device, or is an image represented by volume data which is output from a Multi Slice CT device and an X-ray cone beam CT device using an X-ray flat panel. In a case where the X-ray CT device or the cone beam CT device is used, for example, dual energy imaging may be performed by the X-ray CT, and an image in which a composition (body composition) of each pixel of the three-dimensional medical image can be identified by an effective atomic number (effective-Z) may be used. In a case where the MRI device is used, the three-dimensional medical image may be an image to which information regarding a composition (body composition) of each pixel of the three-dimensional medical image such as fat or lactic acid is added.

The region-of-interest extraction unit 626 extracts region-of-interest information using the region-of-interest learning model 92, for example, based on the endoscopic image output from the acquisition unit 621. The region-of-interest extraction unit 626 inputs the endoscopic image to the region-of-interest learning model 92 and acquires the region-of-interest information output from the region-of-interest learning model 92, thereby extracting the region-of-interest information. The region-of-interest information may include, for example, a type of a region of interest (ROI type), a position of the region of interest (ROI position) in the endoscopic image, and a name of an intracorporeal site where the region of interest is located. The region-of-interest extraction unit 626 outputs the S coordinate and the bending history of the endoscopic image including the region of interest (ROI) to the viewpoint position deriving unit 622. That is, the region-of-interest extraction unit 626 performs filter processing of extracting the endoscopic image including the region of interest from among a plurality of endoscopic images sequentially output from the processor 20 for an endoscope (image processing unit), and outputting the S coordinate and the bending history of the endoscopic image including the region of interest.

Based on the S coordinate and the bending history information output from the region-of-interest extraction unit 626, the viewpoint position deriving unit 622 derives a coordinate (a coordinate in the in-vivo coordinate system) of the three-dimensional medical image corresponding to the S coordinate and the bending history information, that is, a viewpoint position at which the distal end portion 443 of the endoscope 40 is located at a time point when an image of the endoscope is captured.

The viewpoint position deriving unit 622 may correct the insertion distance (S coordinate) based on the acquired bending history information, and derive the viewpoint position based on the corrected insertion distance (S coordinate). The viewpoint position deriving unit 622 detects a shape of the insertion portion 44 (for example, rightward bending by 30 degrees or the like) by arithmetic processing according to the bending angle and the bending direction. The control unit 21 recalculates (corrects) the S coordinate that is the insertion distance based on the detected shape of the insertion portion 44.

Figure 8:
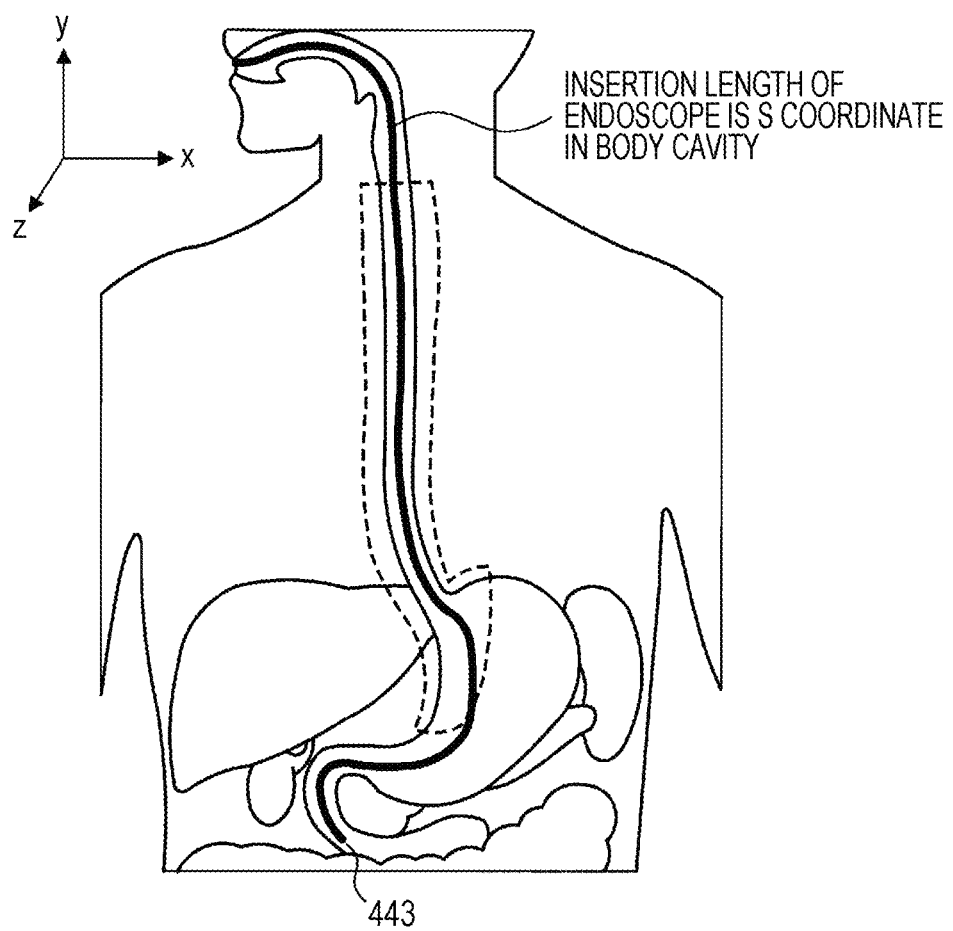
FIG. 8 is an explanatory diagram illustrating an insertion distance (a value of an S coordinate) of an endoscope.

FIG. 8 is an explanatory diagram illustrating the insertion distance (value of the S coordinate) of the endoscope. As illustrated in the drawing, a digestive organ captured by the endoscope 40 is represented by a three-dimensional shape in the three-dimensional medical image. A space is formed inside an inner wall of the digestive organ, and the space serves as an insertion path through which the endoscope is inserted. The S coordinate, which is the insertion distance of the endoscope 40, corresponds to a location which is on the inner side of the insertion path (the inner side of the inner wall of the digestive organ) and in which a path length of the insertion path is substantially equal to the insertion distance. Thus, the coordinate of the distal end portion 443 of the endoscope 40 located on the inner side of the inner wall of the digestive organ can be derived based on the S coordinate. The viewpoint position deriving unit 622 outputs information regarding the derived viewpoint position to the virtual endoscopic image generation unit 623.

Although the viewpoint position deriving unit 622 corrects the viewpoint position based on the bending history acquired from the processor 20 for an endoscope, the present invention is not limited thereto. The control unit 21 of the processor 20 for an endoscope may correct the insertion distance based on the acquired bending history information, and output the corrected insertion distance to the information processing device 6. The acquisition unit 621 may acquire the viewpoint position corrected based on the bending history information by the control unit 21 of the processor 20 for an endoscope.

The position information for associating the endoscopic image with the three-dimensional medical image is derived based on the information regarding the bending history, the information regarding the insertion distance (S coordinate), and the length of the insertion path of the endoscope 40 that is specified in the three-dimensional medical image. The accuracy of the insertion distance (S coordinate) can be improved by correcting the information regarding the insertion distance based on the information regarding the bending history. Therefore, it is possible to accurately specify the viewpoint position (coordinate) and the viewpoint direction (rotation angle) of the endoscope 40 in the coordinate system of the three-dimensional medical image at the time point when the endoscopic image is captured, and to efficiently generate a suitable virtual endoscopic image. Thus, it is possible to further improve the accuracy in association between the endoscopic image and the three-dimensional medical image.

The virtual endoscopic image generation unit 623 generates a virtual endoscopic image based on the acquired three-dimensional medical image and the viewpoint position acquired from the viewpoint position deriving unit 622. The virtual endoscopic image is an image which is generated (reconstructed) based on the three-dimensional medical image obtained by capturing a tubular organ such as a trachea and a bronchus or an intestinal tract by X-ray CT, MRI, or X-ray cone beam CT and in which the inside of an organ (the inside of a body cavity) in the three-dimensional medical image is represented by a virtual endoscope. For example, CT imaging may be performed in a state where air is introduced into a large intestine, and a virtual endoscopic image of the large intestine may be generated (reconstructed) by performing volume rendering on a three-dimensional medical image obtained by the imaging from the inner side of the large intestine.

The virtual endoscopic image generation unit 623 extracts voxel data of the organ in the subject from the acquired three-dimensional medical image. Examples of the organ include a large intestine, a small intestine, a kidney, a bronchus, a blood vessel, and the like. On the other hand, the organ is not limited thereto, and may be another organ. Note that it is assumed that voxel data of the large intestine is extracted and acquired in the present embodiment. As a method of extracting a large intestine region, specifically, first, processing of reconstructing a plurality of axial images of cross sections perpendicular to a body axis based on the three-dimensional medical image, obtaining a boundary between a body surface and the inside of the body using an X-ray CT value based on an X-ray absorption coefficient as a threshold by a known method for each of the axial images, and separating an extracorporeal region and an intracorporeal region from each other with the body surface as a reference is performed. For example, binarization processing using the X-ray CT value is performed on the reconstructed axial image, a contour is extracted by contour extraction processing, and the inside of the extracted contour is extracted as the intracorporeal (human body) region. Next, binarization processing using a threshold is performed on the axial image of the intracorporeal region to extract a candidate for a region of the large intestine in each of the axial images. Specifically, the binarization processing is performed by setting a threshold (for example, −600 HU (Hounsfield Unit) or less) corresponding to a CT value of air since air is present in a tube of the large intestine, and an air region in the body in each of the axial images is extracted as the candidate for the region of the large intestine. The virtual endoscopic image generation unit 623 reconstructs, as the virtual endoscopic image, an image obtained by central projection of projecting, on a predetermined projection plane, voxel data in a plurality of light beam directions radially extending around a line-of-sight vector based on the viewpoint position and a rotation angle that is set as a line-of-sight direction. Note that, as a specific method of the central projection, for example, a known volume rendering method or the like can be used.

For example, the virtual endoscopic image generation unit 623 sequentially generates a plurality of candidate virtual endoscopic images by changing a viewpoint direction, that is, a rotation angle ($\Theta x$, $\Theta y$, $\Theta z$) in the coordinate system of the three-dimensional medical image, for example, by a predetermined unit amount of 1°, with a viewpoint position corresponding to the coordinate of the distal end portion 443 of the endoscope 40 as a starting point. That is, for example, the virtual endoscopic image generation unit 623 may generate the plurality of virtual endoscopic images by projecting a three-dimensional shape of the inner wall of the digestive organ from the viewpoint position inside the digestive organ specified in the three-dimensional medical image using a plurality of rotation angles set as the viewpoint direction. The virtual endoscopic image generation unit 623 outputs each of the plurality of generated virtual endoscopic images in association with the viewpoint direction (rotation angle) used at the time of generating the virtual endoscopic image to the matching degree determination unit 624.

Based on the endoscopic image including the region of interest (ROI) extracted by the region-of-interest extraction unit 626, and the plurality of virtual endoscopic images and the viewpoint directions (rotation angles) used at the time of generating the respective virtual endoscopic image, acquired from the virtual endoscopic image generation unit 623, the matching degree determination unit 624 specifies a virtual endoscopic image that matches with the acquired endoscopic image the most and a viewpoint direction (rotation angle) used at the time of generating the most matching virtual endoscopic image. The matching degree determination unit 624 compares the acquired endoscopic image with each of the plurality of virtual endoscopic images to derive the degree of matching between the endoscopic image and the virtual endoscopic image.

For example, the matching degree determination unit 624 may measure the degree of matching by using an index indicating a correlation between a shadow image of the endoscopic image and a shadow image of the virtual endoscopic image. In order to quantitatively determine the degree of matching between the virtual endoscopic image and the endoscopic image, a level of the degree of matching may be determined based on the degree of the correlation of shadow image information obtained from luminance information. Alternatively, the degree of matching may be determined based on a similarity between the endoscopic image and the virtual endoscopic image. In order to measure the degree of matching between the endoscopic image and the virtual endoscopic image, for example, a method based on AI such as a deep convolutional neural network (DCNN) implemented by a VGG 16 model (caffemodel: VGG_ILSVRC_16_layers) may be used. Alternatively, the matching degree determination unit 624 may compare a similarity between each of the plurality of constructed virtual endoscopic images and the endoscopic image. The comparison of the similarity between the two images is performed by known image processing, and either matching of pixel data levels or matching of levels of features extracted from the images may be used. The matching degree determination unit 624 outputs the virtual endoscopic image specified as having the highest degree of matching with the endoscopic image and the viewpoint direction (rotation angle) used to generate the virtual endoscopic image to the DB registration unit 625. Since the endoscopic image includes the region of interest (ROI), the virtual endoscopic image having the highest degree of matching with the endoscopic image also includes the region of interest (ROI).

Although the matching degree determination unit 624 specifies the virtual endoscopic image having the highest degree of matching with the acquired endoscopic image in the present embodiment, the present invention is not limited thereto. The matching degree determination unit 624 may specify a virtual endoscopic image of which the degree of matching is equal to or higher than a predetermined value as a virtual endoscopic image that can be regarded to be substantially identical to the acquired endoscopic image, and output the virtual endoscopic image to the DB registration unit 625. Since the virtual endoscopic image of which the degree of matching is equal to or higher than the predetermined value is specified, it is unnecessary to perform comparison with all the virtual endoscopic images generated as candidates, so that it is possible to reduce a calculation load and a processing time of the information processing device 6.

In a case where the degree of matching is not equal to or higher than the predetermined value, the matching degree determination unit 624 may generate (reconstruct) a plurality of virtual endoscopic images again from a viewpoint position obtained by finely correcting the viewpoint position acquired from the viewpoint position deriving unit 622, derive the degree of matching between each of the plurality of reconstructed virtual endoscopic images and the endoscopic image, and specify a virtual endoscopic image having the highest degree of matching. In this case, the matching degree determination unit 624 outputs, to the DB registration unit 625, the virtual endoscopic image having the highest degree of matching, and the finely corrected viewpoint position and a viewpoint direction which have been used to generate the virtual endoscopic image.

The acquisition unit 621 outputs the acquired subject ID, the examination date and time, the endoscopic image, and the three-dimensional medical image to the DB registration unit 625. The region-of-interest extraction unit 626 outputs the extracted region-of-interest information (ROI type and ROI position) to the DB registration unit 625. In a case where the endoscopic image is a moving image, the acquisition unit 621 outputs a frame number of the endoscopic image to the DB registration unit 625 in accordance with the endoscopic image. The endoscopic image is the endoscopic image including the region of interest (ROI) extracted by the region-of-interest extraction unit 626.

The DB registration unit 625 registers the acquired subject ID, the examination date and time, the endoscopic image (assigned with the frame number in the case of the moving image), the S coordinate, the three-dimensional medical image, the viewpoint position acquired from the viewpoint position deriving unit 622, the virtual endoscopic image acquired from the matching degree determination unit 624, and the viewpoint direction (rotation angle), and the region-of-interest information (ROI type and ROI position) in the endoscopic image DB 631 in association with each other, thereby storing these pieces of data. The DB registration unit 625 may register the region-of-interest information in the endoscopic image DB 631 in association with pixels corresponding to the region of interest included in the virtual endoscopic image. The DB registration unit 625 may further register three-dimensional coordinates (in-vivo coordinates in the three-dimensional medical image) corresponding to the pixels of the virtual endoscopic image in the endoscopic image DB 631 in association. The region-of-interest extraction unit 626 may derive a name of an intracorporeal site as the region of interest in addition to the ROI type and the ROI position, and the DB registration unit 625 may also register the name (large intestine colon, stomach, duodenum, esophagus, or the like) of the intracorporeal site as the region of interest in the endoscopic image DB 631 in association. When the endoscopic image, the three-dimensional medical image, the virtual endoscopic image, and the like are registered in association with the name of the intracorporeal site as the region of interest in this manner, it is possible to efficiently search for the region of interest based on the name of the intracorporeal site. The DB registration unit 625 registers the endoscopic image including the region of interest (ROI) and the like in the endoscopic image DB 631, but is not limited thereto, and may also register an endoscopic image not including a region of interest (ROI) and position information of the endoscopic image in association with the three-dimensional medical image and the like.

In the present embodiment, the respective functional units in a series of processing have been described while being divided into each functional unit implemented by the control unit 21 of the processor 20 for an endoscope and each functional unit implemented by the control unit 62 of the information processing device 6, but the division of these functional units is an example and is not limited thereto. The control unit 21 of the processor 20 for an endoscope may function as all the functional units implemented by the control unit 62 of the information processing device 6. That is, the processor 20 for an endoscope may substantially include the information processing device 6. Alternatively, the control unit 21 of the processor 20 for an endoscope may only output the captured image captured by the image sensor, and the control unit 62 of the information processing device 6 may function as all the functional units that perform the subsequent processing. Alternatively, the control unit 21 of the processor 20 for an endoscope and the control unit 62 of the information processing device 6 may perform, for example, inter-process communication, thereby functioning in cooperation as the respective functional units in the series of processing.

Figure 9:
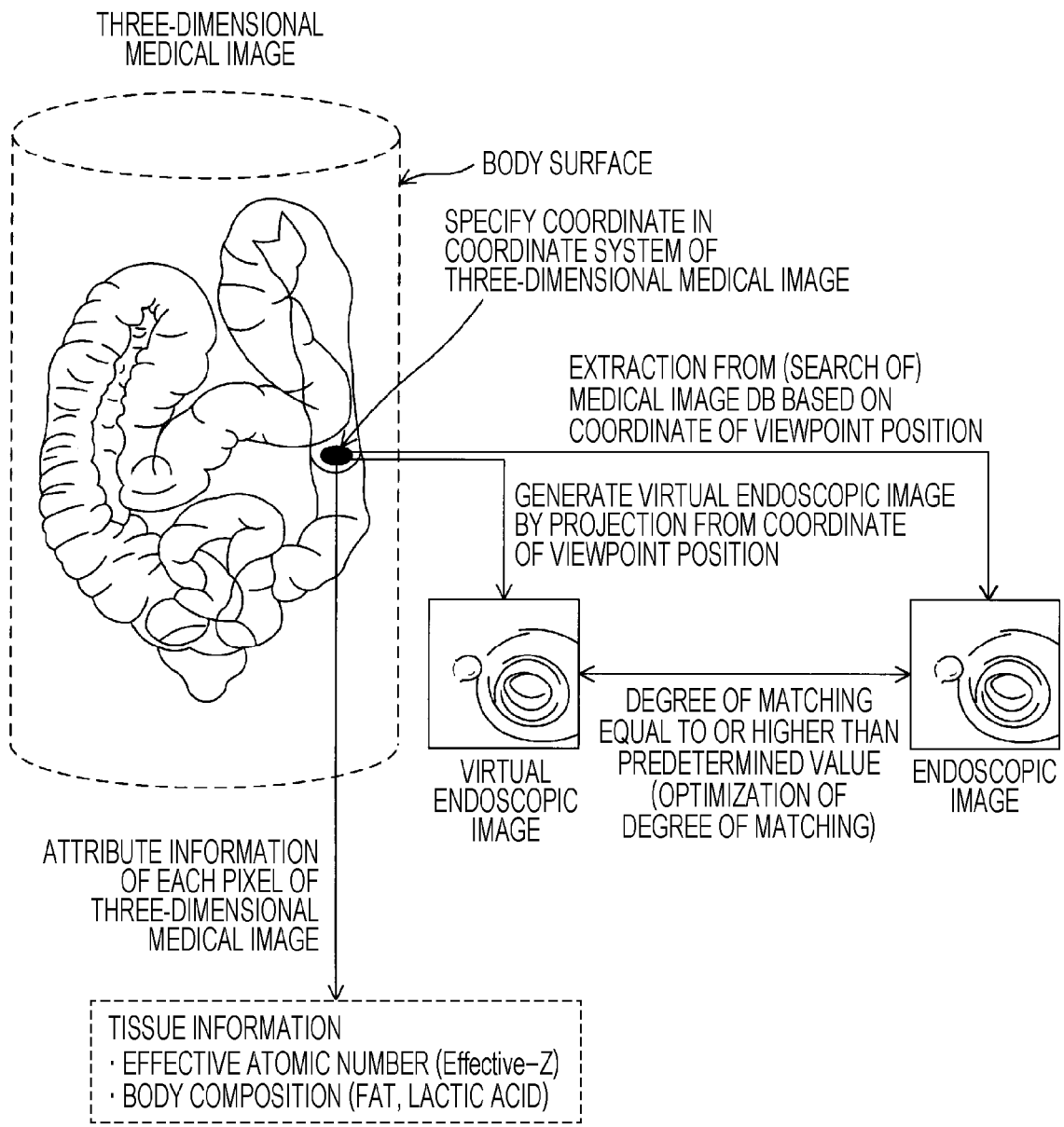
FIG. 9 is an explanatory diagram regarding a relation between an endoscopic image and a three-dimensional medical image.

FIG. 9 is an explanatory diagram regarding a relation between the endoscopic image and the three-dimensional medical image. In FIG. 9, a relationship among the three-dimensional medical image, the virtual endoscopic image, and the endoscopic image is represented in an object-oriented manner.

As described above, the three-dimensional medical image, the virtual endoscopic image, and the endoscopic image including the region of interest (ROI), which are registered in the endoscopic image DB 631, are associated with each other based on the viewpoint position and the viewpoint direction at the capturing time point of the endoscopic image. The viewpoint position corresponds to a coordinate (x, y, z) in the coordinate system (in-vivo coordinate system) of the three-dimensional medical image. The viewpoint direction corresponds to a rotation angle (Θx, Θy, Θz) in an x-axis, a y-axis, and a z-axis in the coordinate system (in-vivo coordinate system) of the three-dimensional medical image.

Each pixel of the endoscopic image corresponds to each pixel of the virtual endoscopic image (virtual endoscopic image that matches with the endoscopic image the most). The virtual endoscopic image is an image generated by performing projection by vector conversion using the viewpoint vector defined by the viewpoint direction (rotation angle) with the viewpoint position based on the three-dimensional medical image as a starting point, and a coordinate in the coordinate system (in-vivo coordinate system) of the three-dimensional medical image is determined by a pixel of the virtual endoscopic image.

As described above, since each of the pixels of the virtual endoscopic image corresponds to each of the pixels of the endoscopic image, it is possible to determine the coordinate of the pixel of the endoscopic image, that is, the coordinate of the intracorporeal site included in the endoscopic image in the coordinate system (in-vivo coordinate system) of the three-dimensional medical image, based on the pixel of the virtual endoscopic image. That is, it is possible to associate the pixel (intracorporeal site) of the endoscopic image with the coordinate in the coordinate system (in-vivo coordinate system) of the three-dimensional medical image by using the virtual endoscopic image as an intermediate medium.

Color information and narrow band pixel information of pixels of the endoscopic image may be added to the three-dimensional medical image, and such a three-dimensional medical image may be registered in the endoscopic image DB 631. In a case where the pixel information of the endoscopic image, such as a difference and the color information, is added to the three-dimensional medical image, it is desirable to perform luminance correction using an imaging light source. As described above, a distance between the pixel of the endoscopic image and the viewpoint position (a point of the imaging light source) is derived on the coordinate system of the three-dimensional medical image. Therefore, luminosity included in the pixel information of the endoscopic image may be corrected based on a reciprocal obtained by squaring the derived distance. In a case where there are a plurality of endoscopic images including pixels located at the same coordinate in the coordinate system of the three-dimensional medical image, the pixel information may be added to the three-dimensional medical image by applying a weight according to the distance by giving preference to an endoscopic image having the shortest distance and calculating a weighted average or a simple average.

In a case where the X-ray CT device or the cone beam CT device is used to capture the three-dimensional medical image, for example, dual energy CT (DECT) imaging may be performed to obtain an image in which a composition (body composition) of each pixel of the three-dimensional medical image can be identified by the effective atomic number (effective-Z). Further, in a case where the MRI device is used, an image, obtained by adding information regarding a composition (body composition) of each pixel of a three-dimensional medical image, such as fat or lactic acid, may be used. When the information regarding the body composition, such as the effective atomic number (effective-Z), fat, or lactic acid, is added to the composition of each pixel of the three-dimensional medical image in this manner, it is possible to provide a doctor or the like with diagnosis support information in which the added information and the endoscopic image associated with the coordinate specified by each pixel of the three-dimensional medical image are associated with each other. Furthermore, as for the intracorporeal site of the region of interest (ROI), for example, in a case where a type of the region of interest is a candidate lesion, it is possible to provide diagnosis support information for determining the severity of tumor depending on whether the vicinity of the candidate lesion is a component close to fat or a component close to water. In addition, a multi-planar reformatted image in the intracorporeal site of the region of interest (ROI) can be generated and provided as the diagnosis support information by using the three-dimensional medical image.

Since the endoscopic image DB 631 is configured in this manner to add the pixel information of the endoscopic image including the region of interest (ROI) to the registered three-dimensional medical image, various types of medical data output from the CT device or the MRI device and the endoscope device 10 can be integrally managed with the region of interest (ROI) as a base axis, searched and extracted from various viewpoints, and the extracted three-dimensional medical image, virtual endoscopic image, endoscopic image, and the like can be provided to the doctor or the like as the diagnosis support information in association with each other.

Figure 10:
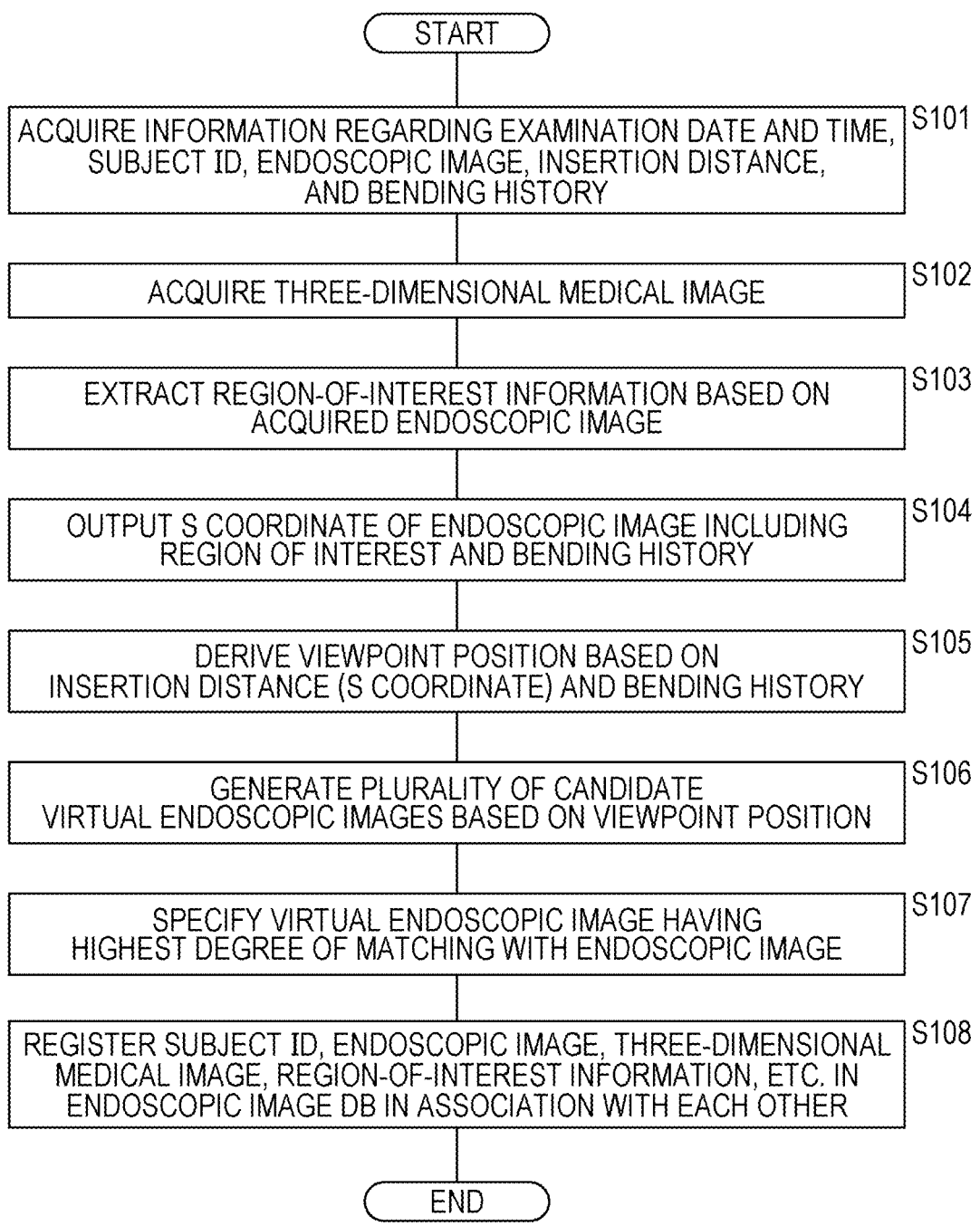
FIG. 10 is a flowchart illustrating an example of a processing procedure performed by the control unit of the information processing device.

FIG. 10 is a flowchart illustrating an example of a processing procedure performed by the control unit 62 of the information processing device 6. For example, the information processing device 6 starts processing of the flowchart based on a content input from the input unit 8 connected to the own device.

The control unit 62 of the information processing device 6 acquires an examination date and time, a subject ID, an endoscopic image, an insertion distance, and information regarding a bending history which are output from the processor 20 for an endoscope (S101). The endoscopic image acquired by the control unit 62 from the processor 20 for an endoscope may be a still image or a moving image. In addition to acquisition of the endoscopic image, the control unit 62 acquires information regarding the insertion distance of the endoscope 40 which is output from the optical sensor or the like, the examination date and time (a capturing date and time of the endoscopic image), and attribute information of a subject such as the subject ID.

The control unit 62 of the information processing device 6 acquires a three-dimensional medical image output from another examination device such as a CT device or an MRI device (S102). The acquisition of the three-dimensional medical image may be performed by the information processing device 6 being communicatively connected to another examination device such as the CT device or the MRI device. Alternatively, in a case where the three-dimensional medical image output from another examination device such as the CT device or the MRI device has already been stored in, for example, an external server (not illustrated), the information processing device 6 may access the external server and acquire the three-dimensional medical image of the subject based on the subject ID output from the processor 20 for an endoscope. Alternatively, the processor 20 for an endoscope may be communicatively connected to another examination device such as the CT device or the MRI device, and the control unit 62 of the information processing device 6 may acquire the three-dimensional medical image from the CT device, the MRI device, or the like via the processor 20 for an endoscope.

The control unit 62 of the information processing device 6 extracts region-of-interest information based on the acquired endoscopic image (S103). The control unit 62 of the information processing device 6 inputs the endoscopic image to the region-of-interest learning model 92 and acquires the region-of-interest information output from the region-of-interest learning model 92, thereby extracting the region-of-interest information. The region-of-interest information includes information regarding a type of a region of interest (ROI type), a position of the region of interest (ROI position) in the endoscopic image, and a name of an intracorporeal site at the position.

The control unit 62 of the information processing device 6 outputs an S coordinate and the bending history of the endoscopic image including the region of interest according to the extracted region-of-interest information (S104). That is, the control unit 62 of the information processing device 6 performs filter processing of extracting the endoscopic image including the region of interest from among a plurality of endoscopic images sequentially output from the processor 20 for an endoscope, and outputting the S coordinate and the bending history of the endoscopic image including the region of interest.

The control unit 62 of the information processing device 6 derives a viewpoint position based on the insertion distance (S coordinate) and the bending history output from the processor 20 for an endoscope (S105). The control unit 62 acquires information regarding the insertion distance (S coordinate) from, for example, the optical sensor or the like arranged inside the insertion portion 44 (flexible tube) of the endoscope 40 via the processor 20 for an endoscope, and derives a coordinate of the distal end portion 443 of the endoscope 40 located on the inner side of the inner wall of the digestive organ into which the endoscope is inserted, based on the acquired insertion distance (S coordinate) and the three-dimensional medical image. The coordinate is a coordinate in the coordinate system (in-vivo coordinate system) of the three-dimensional medical image when a predetermined point is set as an origin. Furthermore, the insertion distance (S coordinate) may be corrected based on the bending history output from the processor 20 for an endoscope to derive the viewpoint position. The control unit 62 calculates a shape of the insertion portion 44 (for example, rightward bending by 30 degrees or the like) by arithmetic processing according to a bending angle and a bending direction included in the bending history, and recalculates (corrects) the S coordinate that is the insertion distance based on the calculated shape of the insertion portion 44. The control unit 62 calculates the viewpoint position based on the corrected insertion distance (S coordinate). Although the position information is derived based on the S coordinate and the bending history of the endoscopic image in the present embodiment, the present invention is not limited thereto. The control unit 62 of the information processing device 6 may acquire only the S coordinate and derive the position information based on the S coordinate.

The control unit 62 of the information processing device 6 generates a plurality of candidate virtual endoscopic images based on the viewpoint position (S106). The control unit 62 sequentially generates the plurality of candidate virtual endoscopic images by changing a viewpoint direction, that is, a rotation angle (Ox, Oy, Oz) in the coordinate system of the three-dimensional medical image by a predetermined unit amount, with the viewpoint position corresponding to the coordinate of the distal end portion 443 of the endoscope 40 as a starting point. For example, in a case where the predetermined unit amount is 10°, the control unit 62 may have 36 resolutions with respect to the rotation angle of each axis, that is, may generate 46656 (36 to the power of 3) candidate virtual endoscopic images.

The control unit 62 of the information processing device 6 specifies a virtual endoscopic image having the highest degree of matching with the endoscopic image among the plurality of generated virtual endoscopic images (S107). For example, the control unit 62 may measure the degree of matching by using an index indicating a correlation between a shadow image of the endoscopic image and a shadow image of the virtual endoscopic image. The control unit 62 specifies the virtual endoscopic image having the highest degree of matching and a viewpoint direction (rotation angle) at the time of generating the virtual endoscopic image. The virtual endoscopic image and the three-dimensional medical image serving as original data of the virtual endoscopic image correspond to each other in the coordinate system (in-vivo coordinate system) of the three-dimensional medical image. Therefore, a coordinate (three-dimensional coordinate) of the region of interest (ROI) in the coordinate system (in-vivo coordinate system) of the three-dimensional medical image is determined based on the region-of-interest information (ROI) included in the virtual endoscopic image. The control unit 62 of the information processing device 6 performs inverse transform of a projection vector, used at the time of generating the virtual endoscopic image from the three-dimensional medical image, for example, on a position of the region of interest included in the virtual endoscopic image, whereby the coordinate (three-dimensional coordinate) in the coordinate system (in-vivo coordinate system) of the three-dimensional medical image of the region of interest is derived.

The control unit 62 of the information processing device 6 registers, in the endoscopic image DB 631, the examination date and time, the subject ID, the endoscopic image, the insertion distance (S coordinate), the three-dimensional medical image, the region-of-interest information (ROI type and ROI position), the three-dimensional coordinate of the ROI, the viewpoint position, the viewpoint direction, and the virtual endoscopic image having the highest degree of matching in association with each other (S108). The control unit 62 registers, in the endoscopic image DB 631, the examination date and time, the subject ID, the endoscopic image, and the insertion distance (S coordinate) acquired from the processor 20 for an endoscope, the three-dimensional medical image acquired from the CT device or the like, the viewpoint position, the virtual endoscopic image having the highest degree of matching, and the viewpoint direction (rotation angles) at the time of generating the virtual endoscopic image in association with each other. All the registered endoscopic images include the region of interest (ROI). Therefore, it is possible to efficiently construct the endoscopic image DB 631 with the region of interest (ROI) as a base axis by registering the information (region-of-interest information) regarding the region of interest (ROI) included in the endoscopic image in association with the above-described endoscopic image, three-dimensional medical image, virtual endoscopic image, and the like.

According to the present embodiment, the information processing device 6 stores the region-of-interest information extracted from the endoscopic image and the three-dimensional medical image in association with each other based on the position information in the coordinate system of the three-dimensional medical image and the respective capturing time points of the endoscopic image and the three-dimensional medical image. Therefore, it is possible to efficiently store the lesion site extracted from the endoscopic image in association with the three-dimensional image obtained by X-ray CT or the like when performing diagnosis support based on the endoscopic image and the three-dimensional medical image. Since the region-of-interest information extracted from the endoscopic image is stored in association with the pixel of the three-dimensional medical image corresponding to the pixel of the virtual endoscopic image of which the degree of matching with the endoscopic image is equal to or higher than the predetermined value, the association between the three-dimensional medical image and the region-of-interest information can be improved, and the diagnosis support information can be efficiently output to the operator of the endoscope 40 such as the doctor.

Second Embodiment

Figure 11:
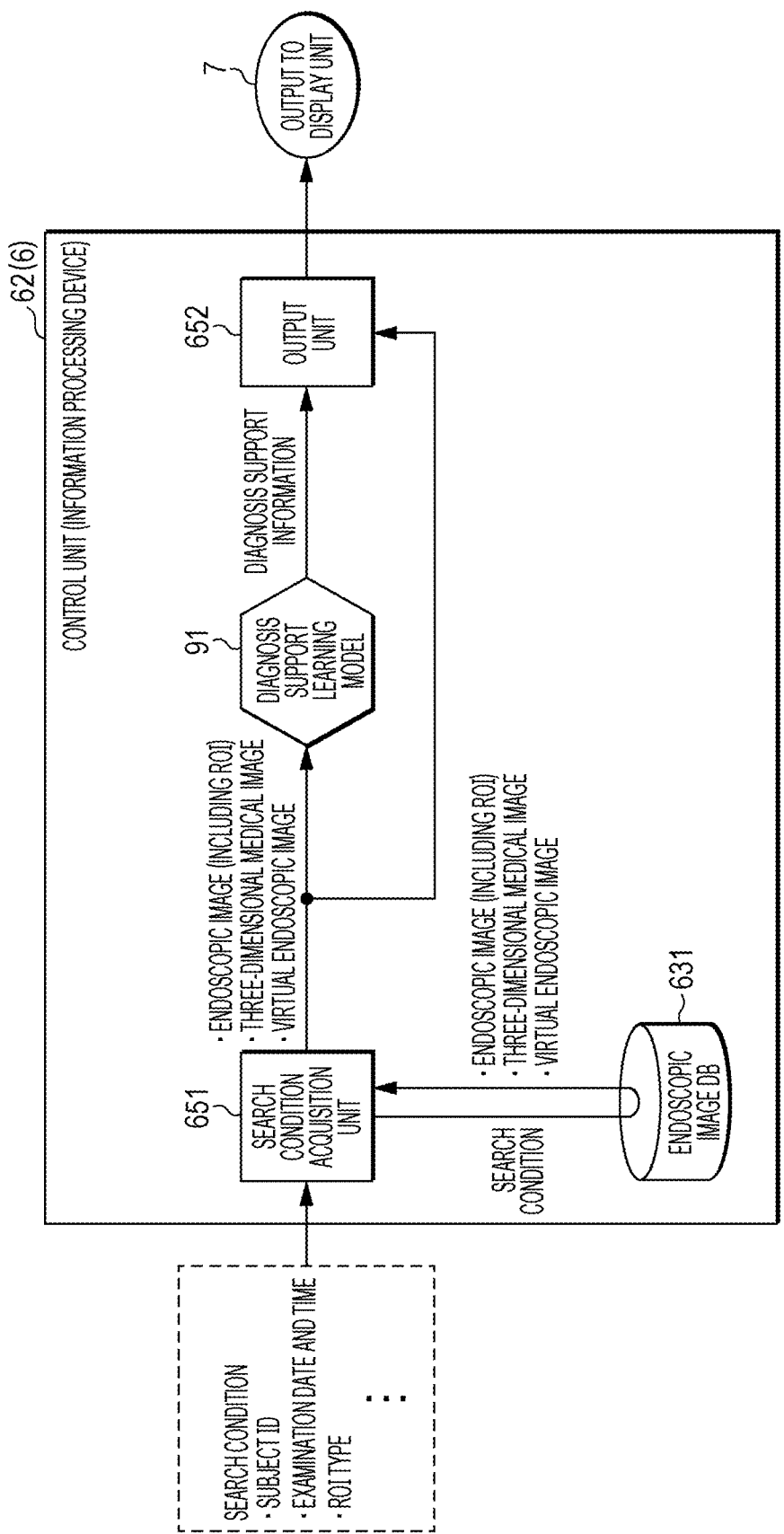
FIG. 11 is a functional block diagram exemplifying functional units included in a control unit of an information processing device according to a second embodiment (search).
Figure 12:
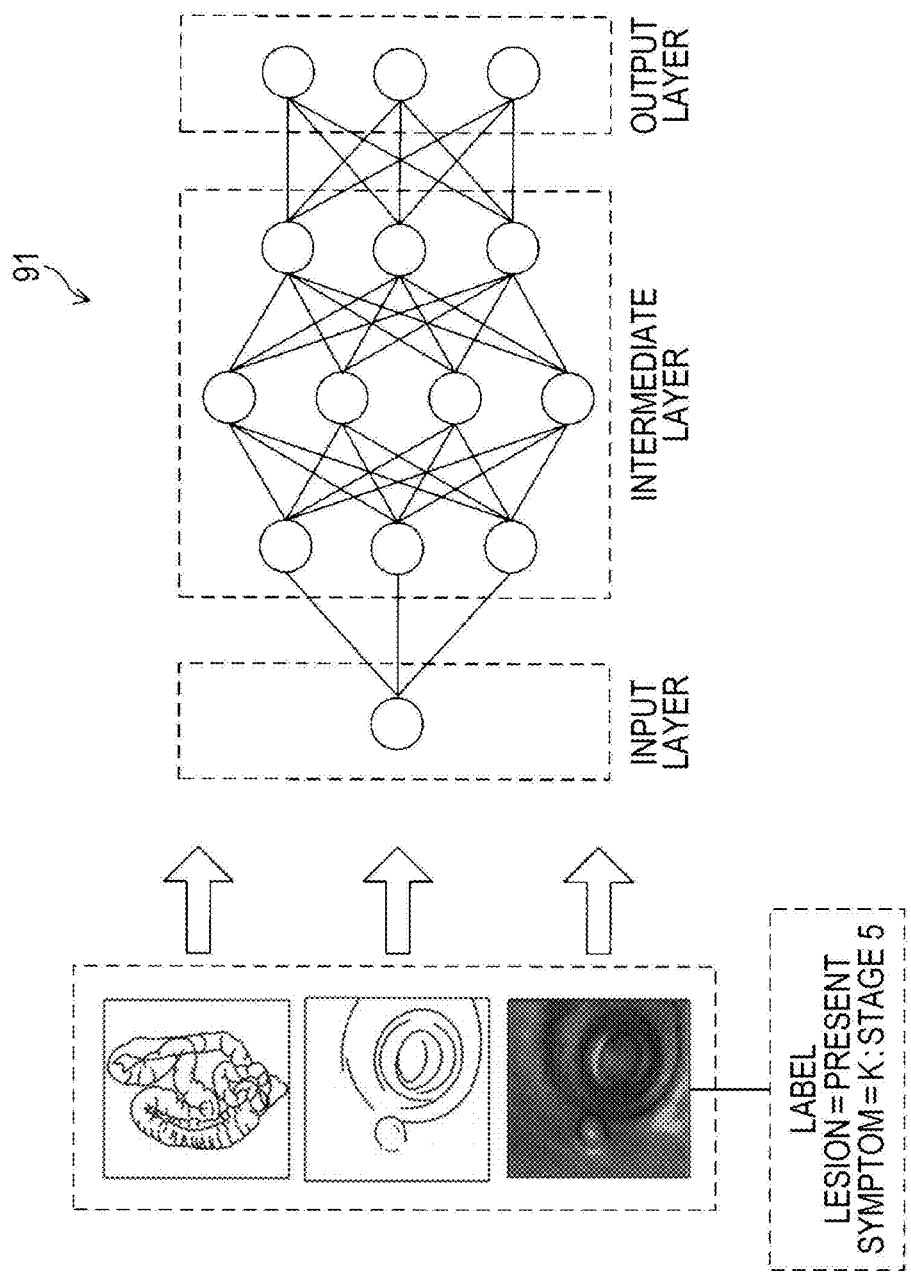
FIG. 12 is an explanatory diagram for describing processing of outputting diagnosis support information using a diagnosis support learning model (learning model).

An information processing device 6 of a second embodiment uses various types of data registered in an endoscopic image DB 631 to output diagnosis support information regarding a region of interest (ROI) included in an endoscopic image registered in the endoscopic image DB 631. FIG. 11 is a functional block diagram exemplifying functional units included in a control unit 62 of the information processing device 6 according to the second embodiment (search). FIG. 12 is an explanatory diagram for describing processing of outputting the diagnosis support information using a diagnosis support learning model 91 (learning model).

The control unit 62 of the information processing device 6 executes a program P stored in a storage unit 63, thereby functioning as a search condition acquisition unit 651 and an output unit 652. In addition, the control unit 62 of the information processing device 6 executes the program P stored in the storage unit 63 or reads an entity file constituting the diagnosis support learning model 91 to function as the diagnosis support learning model 91.

The diagnosis support learning model 91 performs learning based on training data with an endoscopic image, a three-dimensional medical image, and a virtual endoscopic image as problem data and diagnosis support information including a detailed symptom, a progress prediction, a coping content, and the like of a region of interest (ROI) included in the endoscopic image as answer data, thereby constructing (generating) a neural network that receives an input of the endoscopic image or the like and outputs the diagnosis support information regarding the region of interest (ROI). The diagnosis support learning model 91 is constructed by, for example, a neural network (NN) such as CNN, RCNN, or RNN, which is similar to the diagnosis support learning model 91 of the first embodiment. The endoscopic image (problem data) used as the training data and the diagnosis support information (answer data) correlated with these pieces of information are stored in a large amount as result data of an endoscopic examination performed in each medical institution as in the first embodiment, and these pieces of result data can be used to generate a large amount of training data for learning the diagnosis support learning model 91.

The search condition acquisition unit 651 receives a subject ID and an examination date and time input through an endoscopic image selection screen 70 or the like to acquire the subject ID and the like. The search condition acquisition unit 651 searches the endoscopic image DB 631 using the acquired subject ID or the subject ID and the examination date and time as search keys to acquire a plurality of data sets each including an endoscopic image including a region of interest (ROI) and a three-dimensional medical image, a virtual endoscopic image, and the like associated with the endoscopic image. The search condition acquisition unit 651 outputs the acquired endoscopic image including the region of interest (ROI), three-dimensional medical image, and virtual endoscopic image to the diagnosis support learning model 91.

The endoscopic image, the three-dimensional medical image, and the virtual endoscopic image output from the search condition acquisition unit 651 are input to the diagnosis support learning model 91. The diagnosis support learning model 91 outputs the diagnosis support information regarding the region of interest (ROI) based on the input endoscopic image, three-dimensional medical image, and virtual endoscopic image.

The output unit 652 associates the diagnosis support information regarding the region of interest (ROI) acquired from the diagnosis support learning model 91 with the endoscopic image, the three-dimensional medical image, and the virtual endoscopic image, which are targets of the diagnosis support information, and outputs screen data constituting a display screen (integrated image display screen 71) for displaying these images to a display unit 7.

Figure 13:
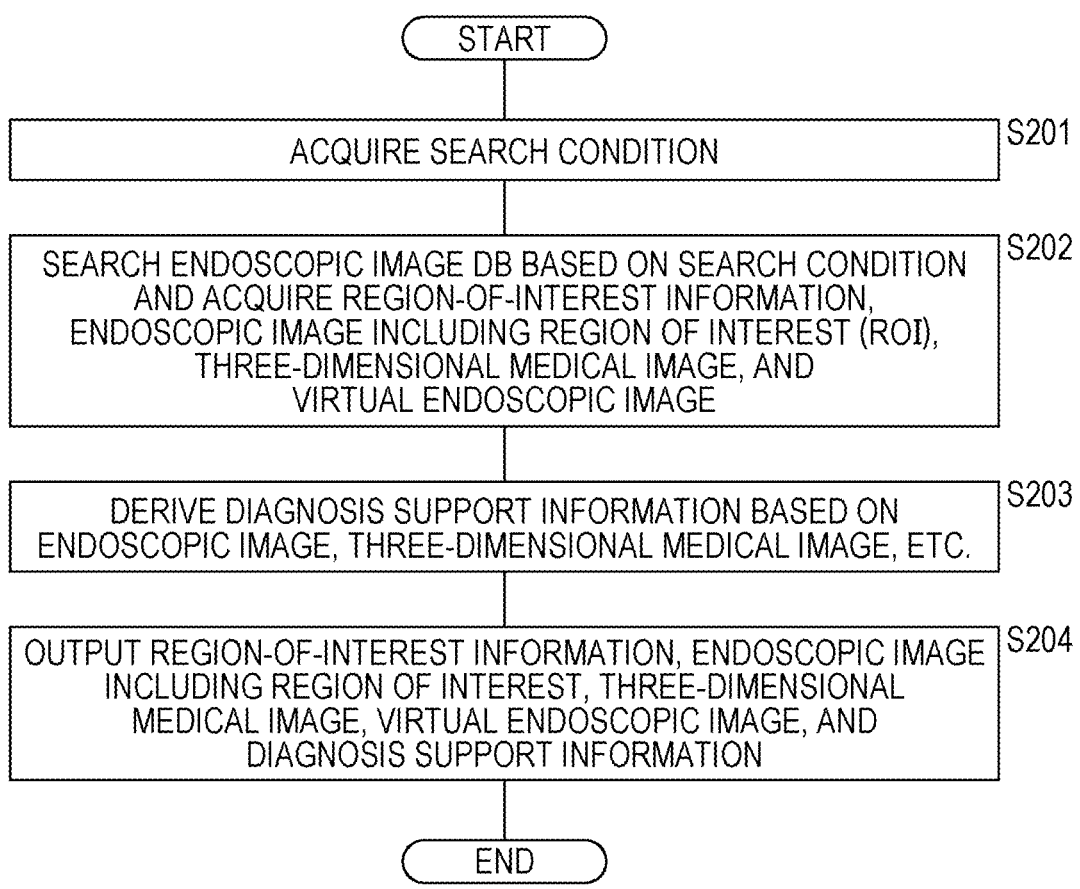
FIG. 13 is a flowchart illustrating an example of a processing procedure performed by the control unit of the information processing device.

FIG. 13 is a flowchart illustrating an example of a processing procedure performed by the control unit 62 of the information processing device 6. For example, the information processing device 6 starts processing of the flowchart based on a content input from the input unit 8 connected to the own device.

The control unit 62 of the information processing device 6 acquires a search condition (S201). The control unit 62 of the information processing device 6 acquires, for example, the search condition input from the input unit 8 of the information processing device 6. Examples of the search condition may include a subject ID of a subject, information regarding an examination date and time, and region-of-interest information.

The control unit 62 of the information processing device 6 searches the endoscopic image DB 631 based on the search condition, and acquires the region-of-interest information, an endoscopic image including a region of interest (ROI), a three-dimensional medical image, and a virtual endoscopic image (S202).

The control unit 62 of the information processing device 6 derives diagnosis support information based on the endoscopic image, the three-dimensional medical image, and the like (S203). For example, the control unit 62 of the information processing device 6 inputs the endoscopic image, the three-dimensional medical image, and the virtual endoscopic image, which are acquired by searching the endoscopic image DB 631, to the diagnosis support learning model 91, and acquires the diagnosis support information output by the diagnosis support learning model 91, thereby deriving the diagnosis support information.

The control unit 62 of the information processing device 6 outputs the region-of-interest information, the endoscopic image including the region of interest (ROI), the three-dimensional medical image, the virtual endoscopic image, and the diagnosis support information (S204). The control unit 62 of the information processing device 6 outputs the region-of-interest information, the endoscopic image including the region of interest (ROI), the three-dimensional medical image, the virtual endoscopic image, and the diagnosis support information to, for example, the display unit 7 connected to the own device. The display unit 7 displays the integrated image display screen 71 as illustrated in the present embodiment based on the information output from the control unit 62.

Figure 14:
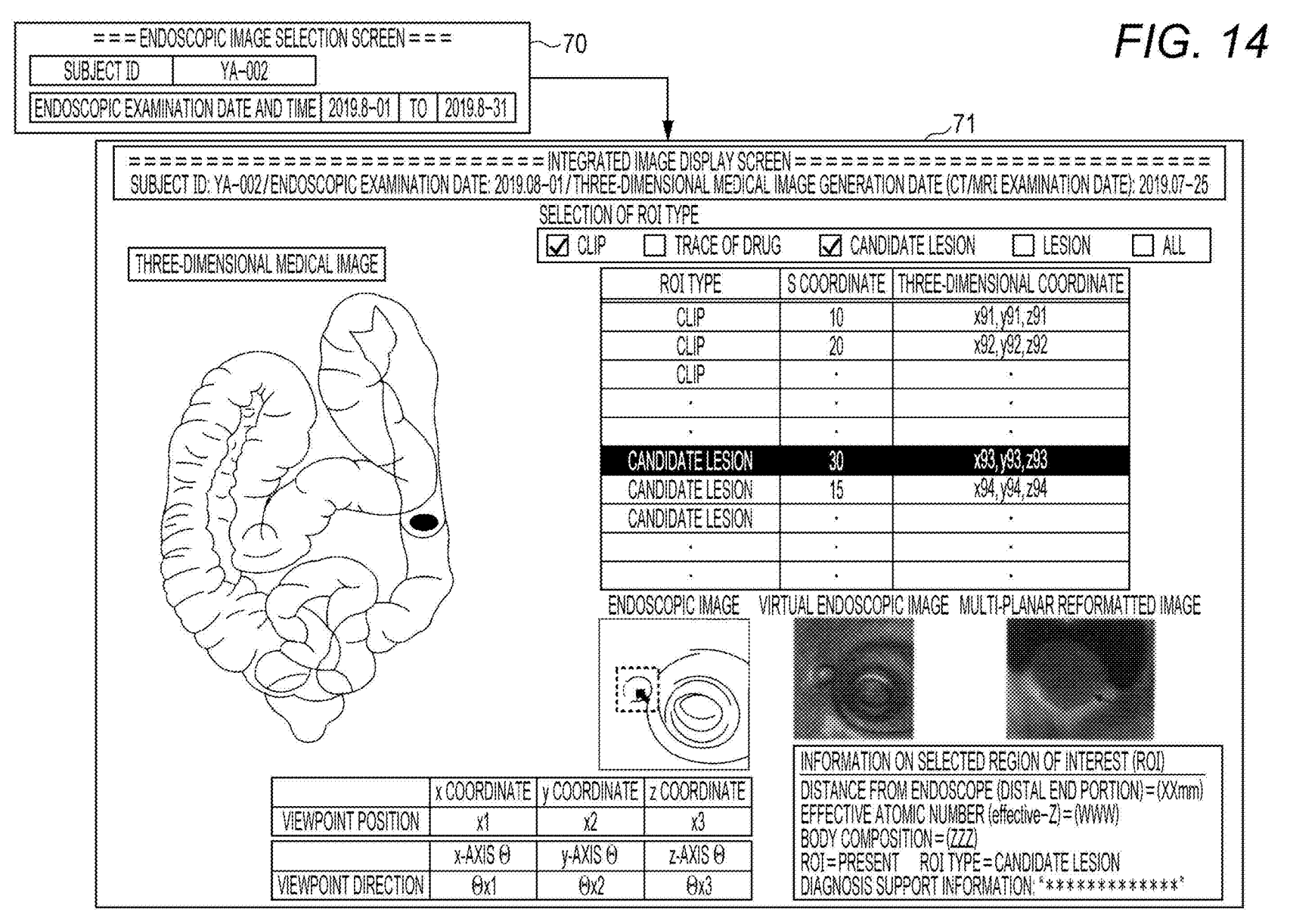

FIG. 14 is an explanatory diagram illustrating an aspect of the integrated image display screen 71. The control unit 62 of the information processing device 6 searches the endoscopic image DB 631 stored in the storage unit 63 to generate the screen data for configuring the display screen (integrated image display screen 71) and output the screen data to the display unit 7, and displays the display screen (integrated image display screen 71) on the display unit 7.

When displaying the integrated image display screen 71, the information processing device 6 displays the endoscopic image selection screen 70 as illustrated in FIG. 14, for example, and receives information serving as a search key such as a subject ID for searching the endoscopic image DB 631. On the endoscopic image selection screen 70, for example, input fields for receiving inputs of the subject ID and an endoscopic examination date and time of the subject are arranged. The information processing device 6 searches the endoscopic image DB 631 based on the subject ID and the like input on the endoscopic image selection screen 70, and displays the integrated image display screen 71 including data of the search result on the display unit 7.

The integrated image display screen 71 includes, for example, a region for displaying bibliographic matters such as a subject ID, a region for displaying a three-dimensional medical image, a region for displaying an endoscopic image, a region for displaying a virtual endoscopic image, a region for displaying a multi-planar reformatted image generated from the three-dimensional medical image, a region for displaying a viewpoint position where an endoscopic image is captured and the like, and a region for displaying information on a selected region of interest (ROI). The integrated image display screen 71 further includes a region for designating a type of a region of interest (ROI) to be included in the endoscopic image, and a region for displaying a list of information (region-of-interest information) regarding the region of interest (ROI) of the designated type.

In the region for displaying bibliographic matters such as a subject ID, the bibliographic matters in data management such as the subject ID, an endoscopic examination date and time, a date of generation of a three-dimensional medical image, and the like used to search the endoscopic image DB 631 are displayed.

In the region for designating a type of a region of interest (ROI), predefined types of the region of interest (ROI types) are displayed in a list, and check boxes and the like for designating any or all of these ROI types are arranged. Although the check box is exemplified as a means for designating the ROI type in the present embodiment, the present invention is not limited thereto, and it goes without saying that a toggle switch, a pull-down, a radio button, or the like may be used.

In the region where the region-of-interest information on the designated ROI type is displayed in a list, the information (region-of-interest information) of the designated region of interest (ROI) is displayed in the form of a list for all the regions of interest (ROI) included in the plurality of endoscopic images acquired from the endoscopic image DB 631 based on the search condition. The region-of-interest information displayed in the form of a list includes the ROI type, the S coordinate of the region of interest, and the three-dimensional coordinate (coordinate in the in-vivo coordinate system of the three-dimensional medical image).

The region where the region-of-interest information is displayed in a list may also be used as a region for selecting any region of interest (ROI) among the plurality of regions of interest (ROI) displayed in the form of a list. In the present embodiment, the selected region of interest (ROI) is highlighted. An endoscopic image, a virtual endoscopic image, a three-dimensional medical image, and a multi-planar reformatted image associated with the selected region of interest (ROI) are displayed on the endoscopic image selection screen 70.

In the region for displaying a three-dimensional medical image, an intracorporeal site such as a digestive organ appearing in the three-dimensional medical image is displayed as a three-dimensional object, and the three-dimensional object can be rotated by dragging any site of the three-dimensional object. The three-dimensional medical image may be displayed in a state where a position of the selected region of interest (ROI) is highlighted, for example.

An endoscopic image including the selected region of interest (ROI) is displayed in the region for displaying an endoscopic image. In the endoscopic image, a frame line for clearly indicating the region of interest (ROI) may be added and displayed. The region of interest (ROI) displayed in the endoscopic image and the region of interest (ROI) displayed in the highlighted state, for example, in the three-dimensional medical image are the same region of interest (ROI).

In the region for displaying a virtual endoscopic image, a virtual endoscopic image having the highest degree of matching with the endoscopic image, which is being displayed in the region for displaying the endoscopic image, is displayed. Since an endoscopic image and a virtual endoscopic image having the highest degree of matching with the endoscopic image are stored in the same record as described above, it is possible to efficiently extract the virtual endoscopic image by using the endoscopic image DB 631. In the region for displaying a multi-planar reformatted image, a multi-planar reformatted image generated from the three-dimensional medical image is displayed. The multi-planar reformatted image shows a cross section in the selected region of interest (ROI).

In the region for displaying a viewpoint position where an endoscopic image is captured, a position (viewpoint position) and a viewpoint direction (rotation angle) of an endoscope 40 in a body at a capturing time point of the endoscopic image, which is being displayed in the region for displaying an endoscopic image, are displayed. That is, a viewpoint position field and a viewpoint direction field are arranged in the region for displaying a viewpoint position where an endoscopic image is captured and the like, and the viewpoint position is displayed in the viewpoint position field and the viewpoint direction is displayed in the viewpoint direction field.

In the region for displaying information on a selected region of interest (ROI), a distance between the intracorporeal site of the selected region of interest (ROI) and a distal end portion 443 of the endoscope 40 is displayed. An endoscopic image and a virtual endoscopic image having the highest degree of matching with the endoscopic image represent a region of the same intracorporeal site, and each pixel of the endoscopic image and each pixel of the virtual endoscopic image substantially match each other or can be regarded as being the same in the coordinate systems in both the images, and thus, correspond to each other. Since the virtual endoscopic image is generated by projecting a three-dimensional medical image or the like, each pixel of the virtual endoscopic image corresponds to a coordinate on the three-dimensional medical image. Therefore, it is possible to specify the coordinate of the intracorporeal site (pixel) in the coordinate system of the three-dimensional medical image based on the intracorporeal site (pixel) included in the selected endoscopic image.

The viewpoint position, which is a position of the distal end portion 443 of the endoscope 40, and a three-dimensional coordinate of the intracorporeal site in the region of interest (ROI) are already registered in a DB registration unit 625. Therefore, the distance between the distal end portion 443 of the endoscope 40 and the intracorporeal site (pixel) included in the selected endoscopic image can be derived based on the three-dimensional coordinate of the intracorporeal site (pixel) in the coordinate system of the three-dimensional medical image and the viewpoint position.

In the region for displaying information on a selected region of interest (ROI), an effective atomic number (effective-Z) of the intracorporeal site (pixel) in the selected region of interest (ROI) or information regarding a body composition such as fat or lactic acid may be displayed. The effective atomic number and the like are attribute information added to each pixel of the three-dimensional medical image. Thus, the pixel of the three-dimensional medical image can be specified based on the coordinate in the coordinate system of the three-dimensional medical image specified as described above, and the effective atomic number and the like added to the pixel can be extracted and displayed.

In the region for displaying information on a selected region of interest (ROI), diagnosis support information regarding the selected region of interest (ROI) may be further displayed. As described above, the diagnosis support information is information output from the diagnosis support learning model 91.

According to the present embodiment, the information processing device 6 searches a plurality of pieces of region-of-interest information and three-dimensional medical images stored in association with each other for specific region-of-interest information and three-dimensional medical image based on the search condition, and outputs the region-of-interest information and the three-dimensional medical image as results of the search, and thus, can efficiently reduce the stored region-of-interest information and three-dimensional medical image. Furthermore, when the region-of-interest information and the three-dimensional medical image to be stored in association with each other are input, the diagnosis support information can be efficiently acquired by using the diagnosis support learning model 91 trained to output the diagnosis support information regarding the region-of-interest information.

Third Embodiment

Figure 15:
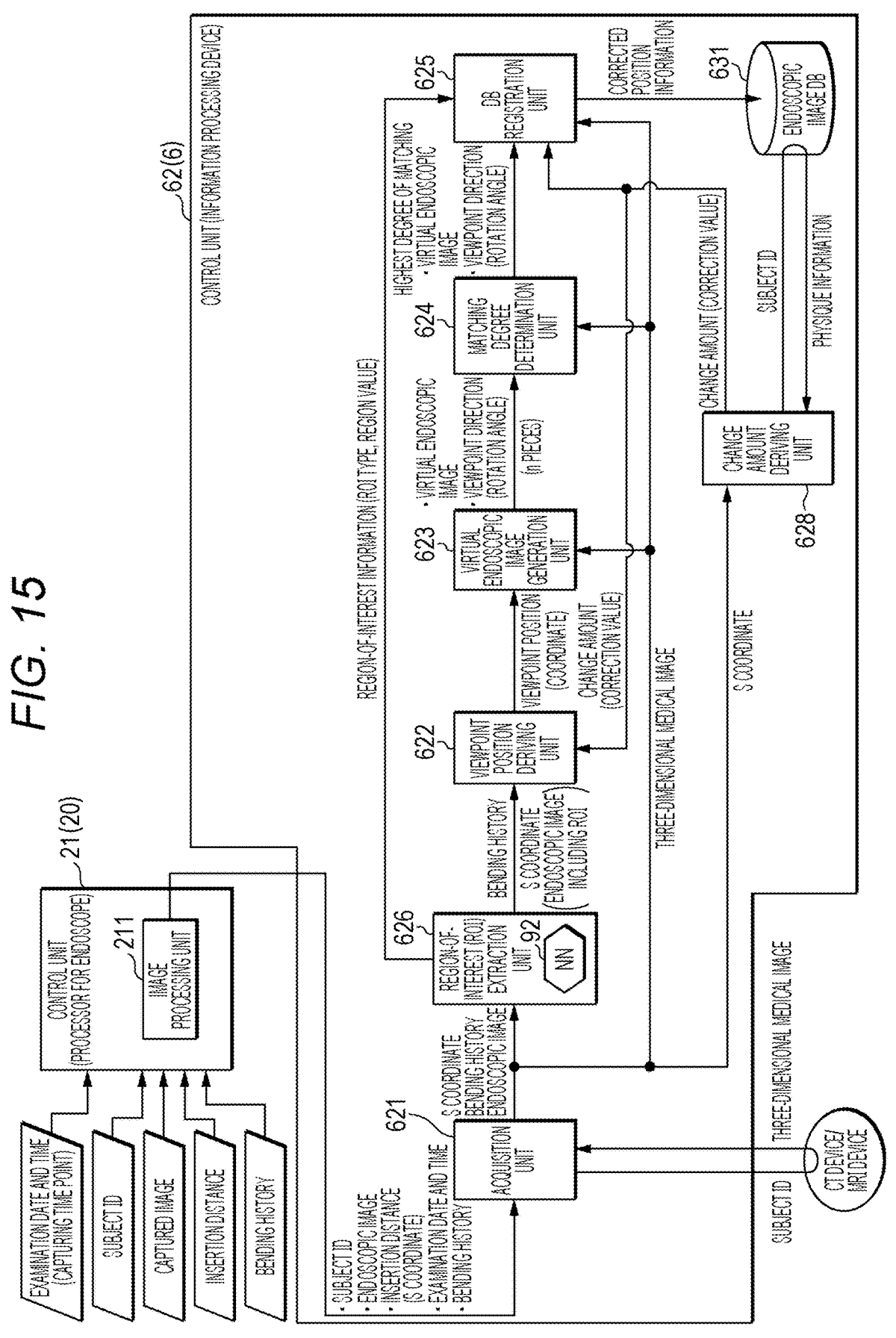

An information processing device 6 of a third embodiment is different from that of the first embodiment in that in terms of including a change amount deriving unit 628 and correcting position information based on a change amount of a physique of a subject. FIG. 15 is a functional block diagram exemplifying functional units included in a control unit 62 of the information processing device 6 according to a third embodiment (correction).

The change amount deriving unit 628 refers to an examination history table included in an endoscopic image DB 631 based on a subject ID output from an acquisition unit 621, and acquires physique information at an examination date and time of each examination type that the subject has undergone. The change amount deriving unit 628 derives the change amount of the physique of the subject based on the acquired physique information at each examination date and time. The physique information may include, for example, a height, a weight, a chest circumference, an abdominal circumference, and a waist circumference, refer to increase or decrease rates of these measured values, and derive a change amount based on the increase or decrease rates.

The change amount deriving unit 628 corrects position information for associating an endoscopic image with a three-dimensional medical image based on the derived change amount. The position information includes an S coordinate, a coordinate (three-dimensional coordinate) of a region of interest (ROI) in a coordinate system (in-vivo coordinate system) of the three-dimensional medical image, a viewpoint position, and a viewpoint direction. The change amount deriving unit 628 may increase a value of the S coordinate (value in the vertical direction) according to the increase rate of the height. Alternatively, the change amount deriving unit 628 may increase or decrease X and Y coordinates (values in the horizontal direction) of a corresponding intracorporeal site according to the increase or decrease rate of the chest circumference, the abdominal circumference, or the waist circumference. The change amount deriving unit 628 outputs the corrected position information such as the S coordinate to related functional units such as a viewpoint position deriving unit 622 and a DB registration unit 625. The viewpoint position deriving unit 622 derives the viewpoint position based on the S coordinate corrected by the change amount deriving unit 628. Each of a virtual endoscopic image generation unit 623 and a matching degree determination unit 624 performs processing similar to that in the first embodiment based on the viewpoint position.

The change amount deriving unit 628 may output the derived change amount to the viewpoint position deriving unit 622, and the viewpoint position deriving unit 622 may correct the S coordinate based on the change amount acquired from the change amount deriving unit 628 and derive the viewpoint position based on the corrected S coordinate. The DB registration unit 625 registers the S coordinate corrected by the change amount deriving unit 628, the coordinate (three-dimensional coordinate) of the region of interest (ROI) in the coordinate system (in-vivo coordinate system) of the three-dimensional medical image, the viewpoint position, and the viewpoint direction in the endoscopic image DB 631.

Figure 16:
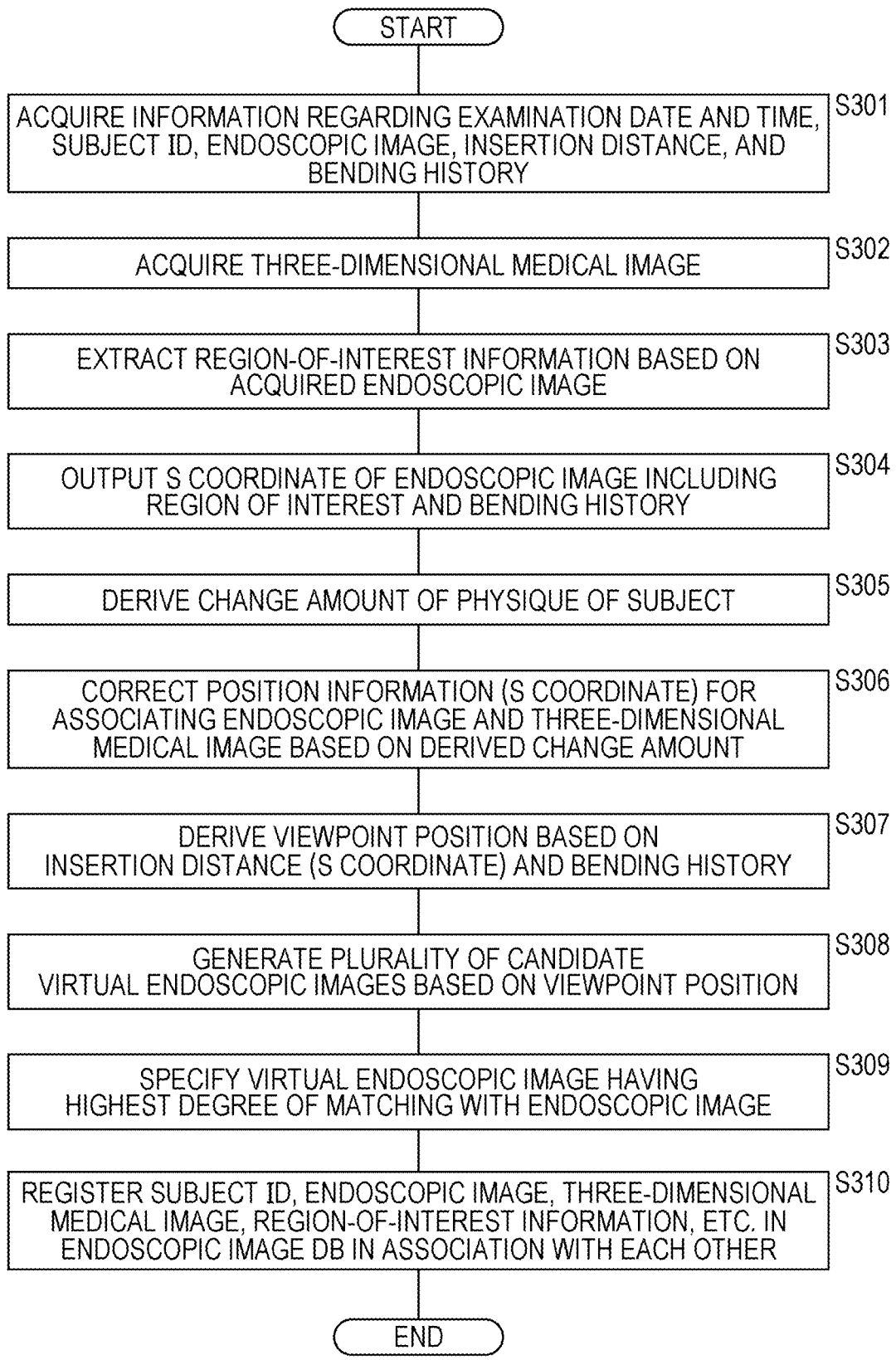
FIG. 16 is a flowchart illustrating an example of a processing procedure performed by the control unit of the information processing device.

FIG. 16 is a flowchart illustrating an example of a processing procedure performed by the control unit 62 of the information processing device 6. For example, the information processing device 6 starts processing of the flowchart based on a content input from the input unit 8 connected to the own device. The control unit 62 of the information processing device 6 performs processing from S301 to S304 similarly to the processing from S101 to S104 of the first embodiment.

The control unit 62 of the information processing device 6 derives a change amount of a physique of a subject (S305). The control unit 62 of the information processing device 6 refers to an examination history table stored in a storage unit 63 based on a subject ID, and derives the change amount of the physique of the subject between an examination date by an endoscope (a capturing date of an endoscopic image) and an examination date by, for example, X-ray CT (a capturing date of an X-ray CT image serving as original data of a three-dimensional medical image). The physique of the subject includes, for example, a height, a weight, a chest circumference, an abdominal circumference, and a waist circumference, and the change amount of the physique may be derived based on change amounts of these measured values.

The control unit 62 of the information processing device 6 corrects position information for associating the endoscopic image with the three-dimensional medical image based on the derived change amount (S306). The position information for associating the endoscopic image with the three-dimensional medical image is, for example, the S coordinate. The control unit 62 of the information processing device 6 corrects the position information with a correction value based on the derived change amount of the physique. For example, the control unit 62 of the information processing device 6 may increase a value of the S coordinate (value in the vertical direction) according to an increase rate of the height.

The control unit 62 of the information processing device 6 performs processing from S307 to S310 similarly to the processing from S105 to S108 of the first embodiment. It goes without saying that the control unit 62 of the information processing device 6 registers the corrected position information when registering the endoscopic image, the three-dimensional medical image, and the position information for associating these images in the endoscopic image DB 631. Although the position information to be corrected based on the change amount of the physique is the S coordinate in the present embodiment, the present invention is not limited thereto. The position information to be corrected based on the change amount of the physique may include, for example, the coordinate (three-dimensional coordinate) of the region of interest (ROI) in the coordinate system (in-vivo coordinate system) of the three-dimensional medical image, the viewpoint position, and the viewpoint direction. The control unit 62 of the information processing device 6 may increase or decrease X and Y coordinates (values in the horizontal direction) of a corresponding intracorporeal site according to an increase or decrease rate of the chest circumference, the abdominal circumference, or the waist circumference.

According to the present embodiment, the change amount of the physique of the subject can be efficiently derived by using at least one of the height, the weight, the chest circumference, the abdominal circumference, and the waist circumference of the subject. Even when there is a difference (period difference) between a capturing time point at which the endoscopic image is captured and a capturing time point at which the three-dimensional medical image is captured and the physique of the physique of the subject has changed in the period, the position information in the coordinate system of the three-dimensional medical image is corrected by the change amount derived based on the difference between the capturing time points. Therefore, the influence of the period difference on the change amount of the physique can be alleviated, and the accuracy of association between region-of-interest information and the three-dimensional medical image can be improved.

Fourth Embodiment

Figure 17:
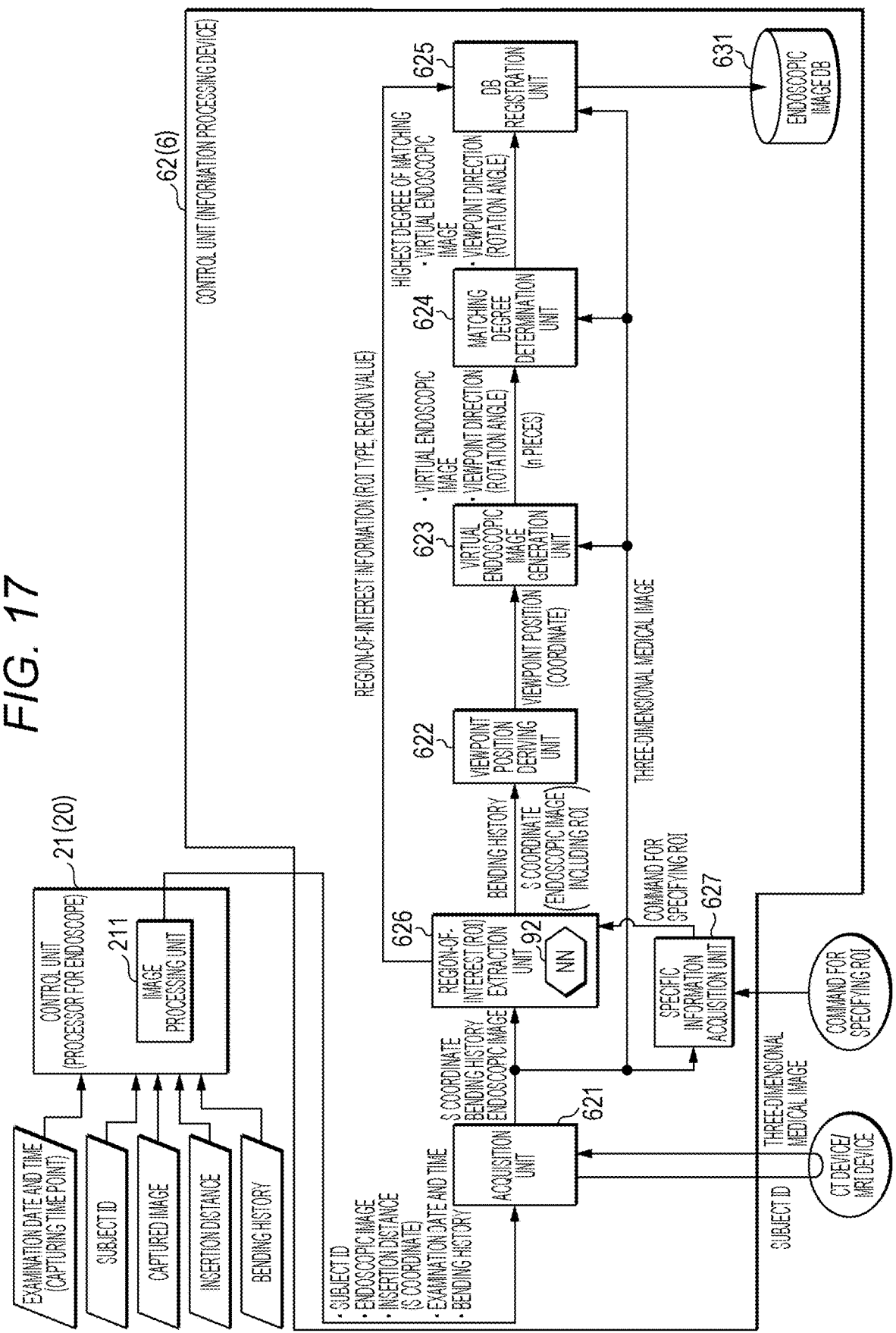
FIG. 17 is a functional block diagram exemplifying functional units included in a control unit of an information processing device according to a fourth embodiment (acquisition of an operation from an operator).

An information processing device 6 of a third fourth embodiment is different from that of the first embodiment in terms of including a specific information acquisition unit 627, acquiring specific information for specifying a region of interest (ROI) according to an operation performed by an operator of an endoscope 40, and extracting information regarding the region of interest (ROI) based on the acquired specific information. FIG. 17 is a functional block diagram exemplifying functional units included in a control unit 62 of the information processing device 6 according to a fourth embodiment (acquisition of an operation from the operator).

The specific information acquisition unit 627 receives the operation performed by the operator of the endoscope 40 such as a doctor, and acquires the specific information input by the operation. For example, the specific information acquisition unit 627 acquires the specific information input from an input unit such as a mouse or a touch panel used by the operator with respect to a displayed endoscopic image. The specific information includes a type and a position of a region of interest (ROI) included in the endoscopic image, and a name of an intracorporeal site.

The specific information acquisition unit 627 outputs the acquired specific information to a region-of-interest extraction unit 626. The region-of-interest extraction unit 626 of the present embodiment extracts the region of interest (ROI) included in the endoscopic image based on the specific information output from the specific information acquisition unit 627, and outputs information (region-of-interest information) on the region of interest (ROI) to related functional units such as a viewpoint position deriving unit 622 as in the first embodiment. Each of the other functional units such as the viewpoint position deriving unit 622 performs processing similar to that of the first embodiment.

Figure 18:
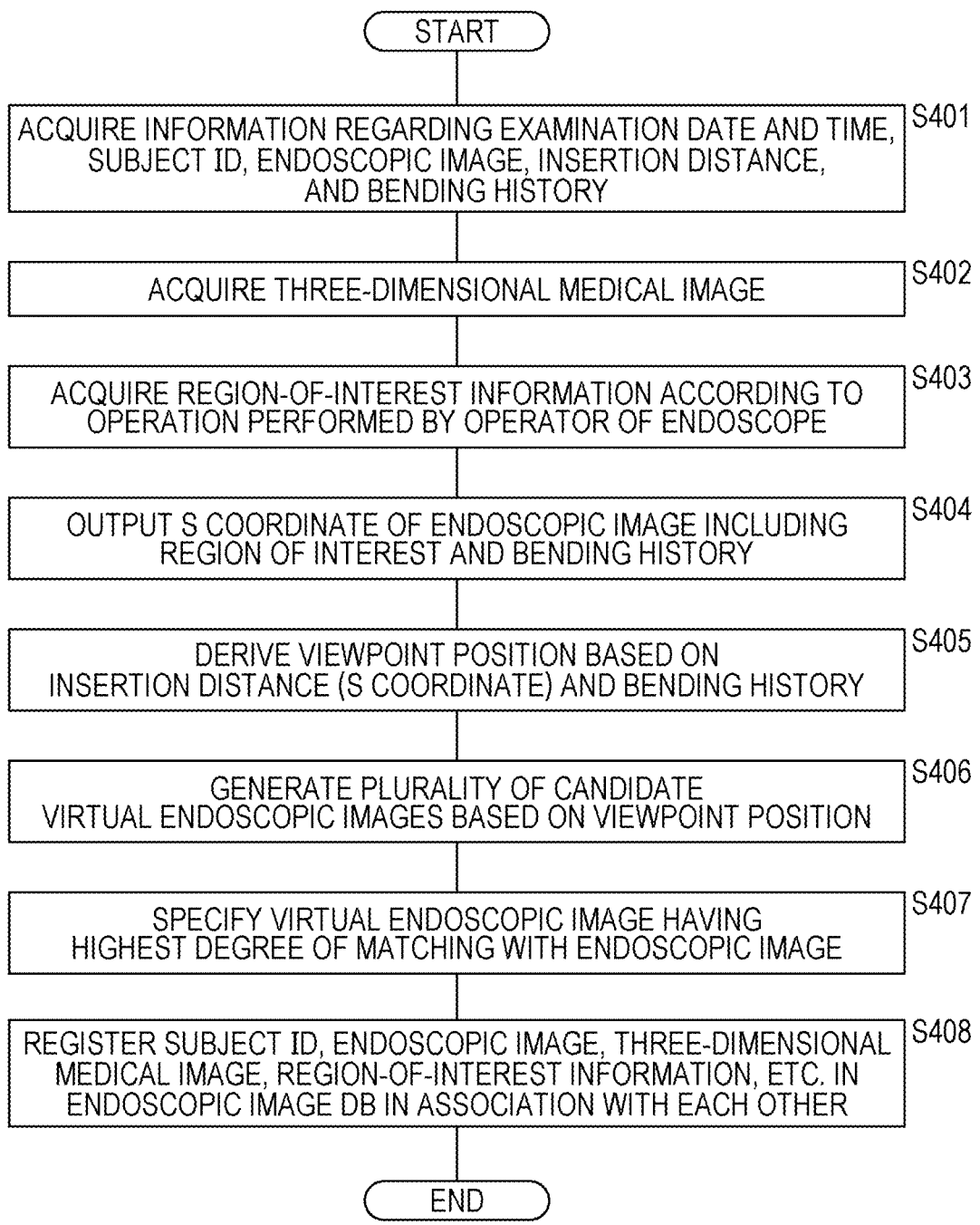
FIG. 18 is a flowchart illustrating an example of a processing procedure performed by the control unit of the information processing device.

FIG. 18 is a flowchart illustrating an example of a processing procedure performed by the control unit 62 of the information processing device 6. For example, the information processing device 6 starts processing of the flowchart based on a content input from the input unit 8 connected to the own device. The control unit 62 of the information processing device 6 performs processing from S401 to S402 similarly to the processing from S101 to S102 of the first embodiment.

The control unit 62 of the information processing device 6 acquires region-of-interest information according to an operation performed by an operator of the endoscope 40 (S403). The control unit 62 of the information processing device 6 receives the operation (region-of-interest specifying operation) from the operator of the endoscope 40, specifies a region of interest (ROI) in an endoscopic image according to the region-of-interest specifying operation, and acquires the region-of-interest information. The region-of-interest specifying operation is, for example, an investigation operation of specifying a position and a type of the region of interest in the endoscopic image displayed on a display unit 7, and is performed using the input unit 8 of the information processing device 6, for example.

The control unit 62 of the information processing device 6 performs processing from S404 to S408 similarly to the processing from S104 to S108 of the first embodiment.

According to the present embodiment, the specific information for specifying the region of interest in the endoscopic image is acquired according to the operation performed by the operator of the endoscope 40 such as the doctor, and thus, the region-of-interest information can be efficiently extracted from the endoscopic image.

Fifth Embodiment

Figure 19:
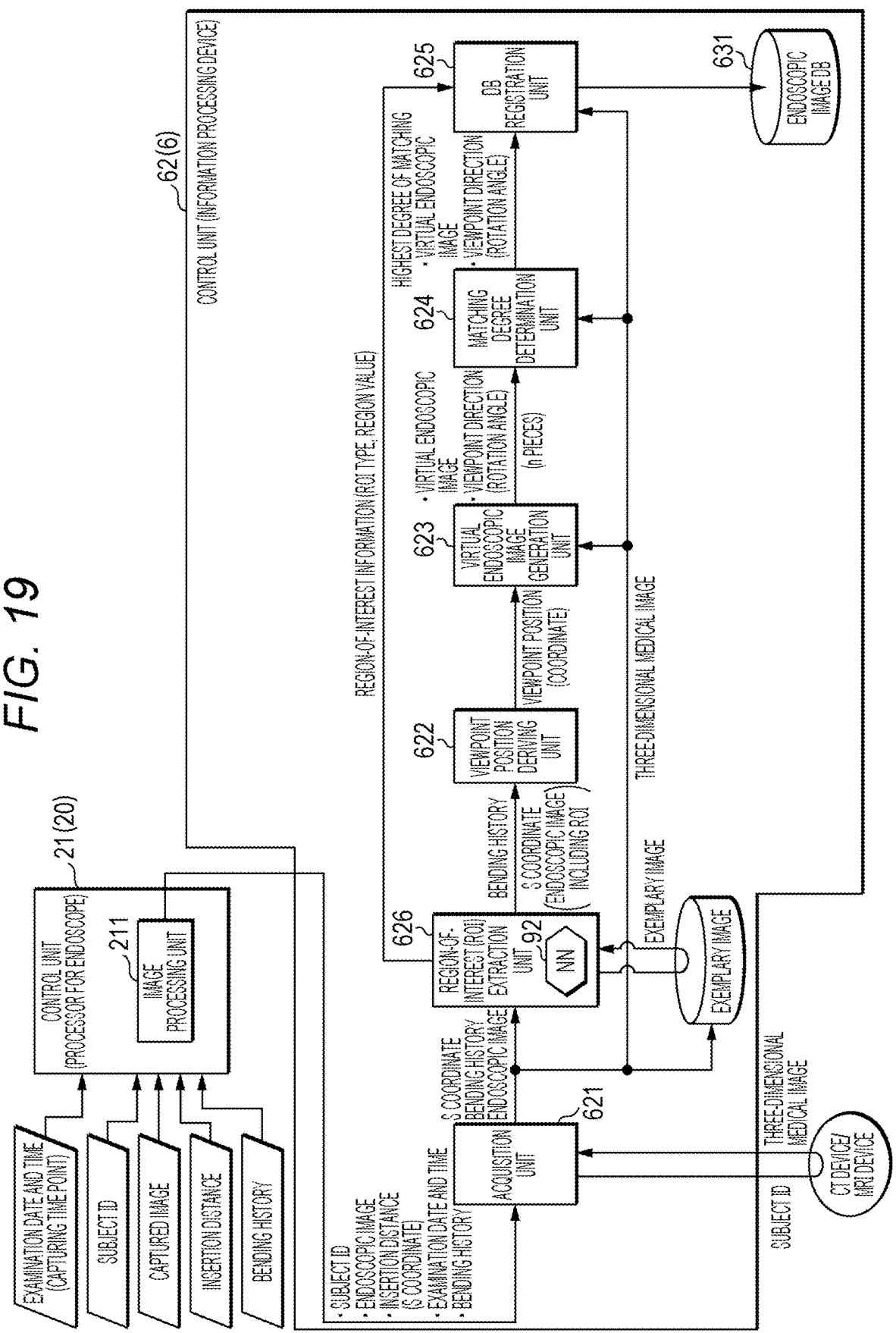
FIG. 19 is a functional block diagram exemplifying functional units included in a control unit of an information processing device according to a fifth embodiment (exemplary image).

A region-of-interest extraction unit 626 of an information processing device 6 of the fifth embodiment is different from that of the first embodiment in terms of extracting region-of-interest information based on a comparison result between an exemplary image registered in advance in a storage unit 63 of the information processing device 6 and an acquired endoscopic image. FIG. 19 is a functional block diagram exemplifying functional units included in a control unit 62 of the information processing device 6 according to a fifth embodiment (exemplary image).

The region-of-interest extraction unit 626 of the present embodiment refers to a plurality of the exemplary images registered in advance in the storage unit 63 of the information processing device 6, and extracts the region-of-interest information based on the comparison result with the acquired endoscopic image. The storage unit 63 of the information processing device 6 stores the plurality of exemplary images of regions of interest (ROI), in association with types of the regions of interest (ROI types) and names of intracorporeal sites of the regions of interest as attribute information of the exemplary images, for example.

The region-of-interest extraction unit 626 performs image processing such as edge detection on the endoscopic image output from an acquisition unit 621, for example, to specify a region in which an image of an intracorporeal site having a characteristic color or shape has been captured, and compares the specified region with the plurality of exemplary images stored in the storage unit 63 using, for example, pattern matching or the like. The region-of-interest extraction unit 626 derives a position (ROI position) of the region in the endoscopic image by edge detection or the like. The region-of-interest extraction unit 626 determines an exemplary image closest to or similar to the specified region, and specifies a type of the region of interest (ROI type) of the region and a name of the intracorporeal site of the region of interest based on accompanying information of the determined exemplary image.

The region-of-interest extraction unit 626 outputs the extracted region-of-interest information to a DB registration unit 625 as in the first embodiment, and outputs an S coordinate of the endoscopic image including the region of interest to other functional units such as a matching degree determination unit 624. Each of the other functional units such as the viewpoint position deriving unit 622 performs processing similar to that of the first embodiment.

Figure 20:
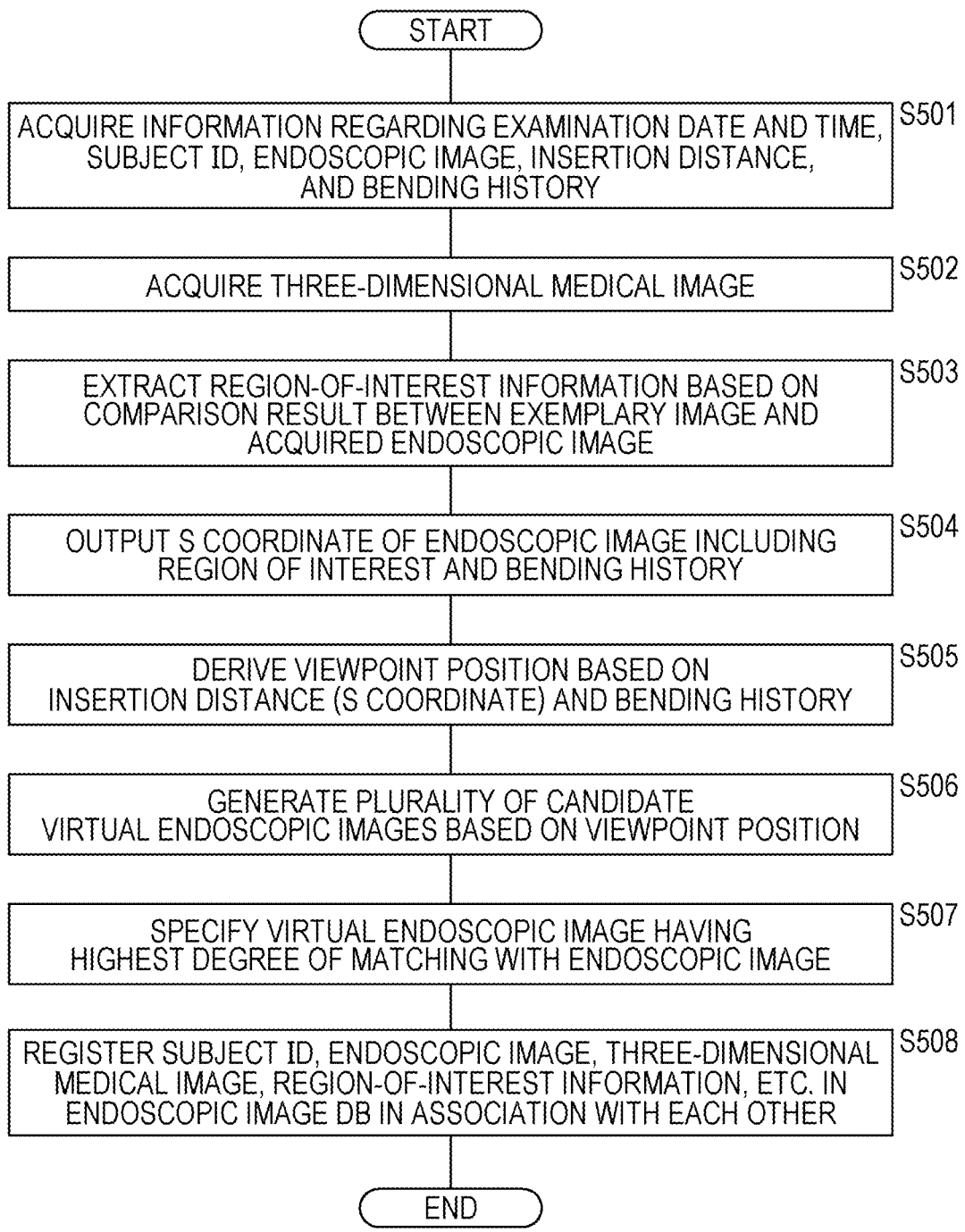
FIG. 20 is a flowchart illustrating an example of a processing procedure performed by the control unit of the information processing device.

FIG. 20 is a flowchart illustrating an example of a processing procedure performed by the control unit 62 of the information processing device 6. For example, the information processing device 6 starts processing of the flowchart based on a content input from the input unit 8 connected to the own device. The control unit 62 of the information processing device 6 performs processing from S501 to S502 similarly to the processing from S101 to S102 of the first embodiment.

The control unit 62 of the information processing device 6 extracts region-of-interest information based on a comparison result between an exemplary image registered in advance and an acquired endoscopic image (S503). The control unit 62 of the information processing device 6 refers to a plurality of the exemplary images registered in advance in the storage unit 63 of the own device, and extracts the region-of-interest information based on the comparison result with the acquired endoscopic image. For example, the control unit 62 of the information processing device 6 performs image processing such as edge detection on the endoscopic image to specify a region where an image of an intracorporeal site having a characteristic color or shape has been captured, and compares the specified region with the plurality of exemplary images by pattern matching or the like. A position (ROI position) of the region in the endoscopic image can be derived by edge detection or the like. An exemplary image closest to or similar to the specified region is determined, and a type (ROI type) of a region of interest in the region is determined based on accompanying information of the determined exemplary image. The control unit 62 of the information processing device 6 extracts the region-of-interest information (ROI position and ROI type) from an endoscopic image by performing the above processing.

The control unit 62 of the information processing device 6 performs processing from S504 to S508 similarly to the processing from S104 to S108 of the first embodiment.

According to the present embodiment, a region of interest is specified from an endoscopic image based on a comparison result of, for example, pattern matching or the like between a predetermined exemplary image registered in advance and the endoscopic image to extract information regarding the specified region of interest, that is, region-of-interest information, and thus, it is possible to efficiently extract the region-of-interest information from the endoscopic image.

The embodiments disclosed herein are considered to be in all respects as illustrative and not restrictive. The technical features described in the embodiments can be combined with each other, and the scope of the present invention is intended to include all modifications within the scope of the claims and the scope equivalent to the claims.

REFERENCE SIGNS LIST

S diagnosis support system
10 endoscope device
15 keyboard
16 storage rack
20 processor for endoscope
21 control unit
211 image processing unit
22 main storage device
23 auxiliary storage device
24 communication unit
25 touch panel
26 display device I/F
27 input device I/F
28 reading unit
31 endoscope connector
311 electrical connector
312 optical connector
33 light source
34 pump
35 water supply tank
36 air/water supply port
40 endoscope
43 operation unit
431 control button
433 bending knob
44 insertion portion (flexible tube)
441 soft portion
442 bending section 443 distal end portion
444 imaging unit
45 bend preventing portion
48 scope connector
49 universal cord
50 display device
6 information processing device
61 communication unit
62 control unit
621 acquisition unit
622 viewpoint position deriving unit
623 virtual endoscopic image generation unit
624 matching degree determination unit
625 DB registration unit
626 region-of-interest extraction unit
627 specific information acquisition unit
628 change amount deriving unit
651 search condition acquisition unit
652 output unit
63 storage unit
631 endoscopic image DB
632 recording medium
P program
64 input/output I/F
7 display unit
70 endoscopic image selection screen
71 integrated image display screen
8 input unit
91 diagnosis support learning model (learning model)
92 region-of-interest learning model (second learning model)

The invention claimed is:

1. A non-transitory computer-readable medium containing a program that causes a computer to perform processing of:
acquiring an endoscopic image obtained by capturing a subject using an endoscope;
extracting, from the acquired endoscopic image, region-of-interest information of a therapeutic clip previously applied to the subject, a trace of a drug previously given to the subject, a candidate lesion, or a lesion;
acquiring a three-dimensional medical image obtained by capturing an inside of a body of the subject using at least one of X-ray CT, X-ray cone beam CT, MRI-CT, and an ultrasonic diagnostic device;
deriving position information in a coordinate system of the three-dimensional medical image specified by the region-of-interest information and the three-dimensional medical image; and
storing the region-of-interest information and the three-dimensional medical image in association with each other based on the derived position information and capturing time points of the endoscopic image and the three-dimensional medical image, wherein
the region-of-interest information is extracted from the endoscopic image based on a comparison result with a predetermined exemplary image stored in advance.

2. The non-transitory computer-readable medium containing a program according to claim 1, wherein
when the region-of-interest information and the three-dimensional medical image stored in association with each other are input, the region-of-interest information and the three-dimensional medical image are input to a learning model trained to output diagnosis support information regarding the region-of-interest information, and
the diagnosis support information output from the learning model is acquired.

3. The non-transitory computer-readable medium containing a program according to claim 1, wherein
a search condition for searching for the region-of-interest information is acquired,
the region-of-interest information and the three-dimensional medical image stored in association with each other are specified based on the acquired search condition, and
the specified region-of-interest information and three-dimensional medical image are output.

4. The non-transitory computer-readable medium containing a program according to claim 1, wherein
a change amount of a physique of the subject is derived based on a difference between the captured time points of the endoscopic image and the three-dimensional medical image,
the position information is corrected based on the derived change amount, and
the region-of-interest information and the three-dimensional medical image are stored in association with each other based on the corrected position information and the captured time points of the endoscopic image and the three-dimensional medical image.

5. The non-transitory computer-readable medium containing a program according to claim 4, wherein
the change amount of the physique of the subject is derived using at least one of a height, a weight, a chest circumference, an abdominal circumference, and a waist circumference of the subject.

6. The non-transitory computer-readable medium containing a program according to claim 1, wherein
information regarding an insertion distance of the endoscope inserted into the body of the subject at a time point when the endoscopic image is captured, and
the deriving of the position information includes processing of deriving the position information in the coordinate system of the three-dimensional medical image based on the information regarding the insertion distance.

7. The non-transitory computer-readable medium containing a program according to claim 6, wherein
information regarding a bending history of the endoscope inserted into the body of the subject is acquired, and
the deriving of the position information includes processing of deriving the position information in the coordinate system of the three-dimensional medical image based on the information regarding the bending history and the information regarding the insertion distance.

8. The non-transitory computer-readable medium containing a program according to claim 1, wherein
the deriving of the position information includes processing of:
generating virtual endoscopic images reconstructed from the three-dimensional medical image;
deriving a degree of matching between each of the generated virtual endoscopic images and the endoscopic image; and
deriving the position information based on a virtual endoscopic image whose degree of matching is equal to or higher than a predetermined value among the virtual endoscopic images, and
the region-of-interest information extracted from the endoscopic image is stored in association with a pixel of the three-dimensional medical image corresponding to a pixel of the virtual endoscopic image whose degree of matching is equal to or higher than the predetermined value.

9. The non-transitory computer-readable medium containing a program according to claim 1, wherein
when the endoscopic image is input, the endoscopic image is input to a second learning model trained to output the region-of-interest information, and
the region-of-interest information output from the second learning model is acquired.

10. The non-transitory computer-readable medium containing a program according to claim 1, wherein
specific information for specifying a region of interest in the endoscopic image is acquired based on an operation performed by an operator of the endoscope, and
the region-of-interest information is extracted from the endoscopic image based on the acquired specific information.

11. The non-transitory computer-readable medium containing a program according to claim 1, wherein the endoscopic image acquired from the endoscope is a still image or a moving image.

12. An information processing method for causing a computer to execute processing of:
acquiring an endoscopic image obtained by capturing a subject using an endoscope;
extracting, from the acquired endoscopic image, region-of-interest information of a therapeutic clip previously applied to the subject, a trace of a drug previously given to the subject, a candidate lesion, or a lesion;
acquiring a three-dimensional medical image obtained by capturing an inside of a body of the subject using at least one of X-ray CT, X-ray cone beam CT, MRI-CT, and an ultrasonic diagnostic device;
deriving position information in a coordinate system of the three-dimensional medical image specified by the region-of-interest information and the three-dimensional medical image; and
storing the region-of-interest information and the three-dimensional medical image in association with each other based on the derived position information and a capturing time point of each of the endoscopic image and the three-dimensional medical image, wherein
the region-of-interest information is extracted from the endoscopic image based on a comparison result with a predetermined exemplary image stored in advance.

13. An information processing device comprising:
an acquisition unit that acquires an endoscopic image obtained by capturing a subject using an endoscope and a three-dimensional medical image obtained by capturing an inside of a body of the subject using at least one of X-ray CT, X-ray cone beam CT, MRI-CT, and an ultrasonic diagnostic device;
an extraction unit that extracts, from the acquired endoscopic image, region-of-interest information of a therapeutic clip previously applied to the subject, a trace of a drug previously given to the subject, a candidate lesion, or a lesion;
a deriving unit that derives position information in a coordinate system of the three-dimensional medical image specified by the region-of-interest information and the three-dimensional medical image; and
a storage unit that stores the region-of-interest information and the three-dimensional medical image in association with each other based on the derived position information and a capturing time point of each of the endoscopic image and the three-dimensional medical image, wherein
the region-of-interest information is extracted from the endoscopic image based on a comparison result with a predetermined exemplary image stored in advance.

* * * * *